US006593111B2

(12) United States Patent
Baric et al.

(10) Patent No.: US 6,593,111 B2
(45) Date of Patent: Jul. 15, 2003

(54) DIRECTIONAL ASSEMBLY OF LARGE VIRAL GENOMES AND CHROMOSOMES

(75) Inventors: Ralph S. Baric, Haw River, NC (US); Boyd Yount, Hillsborough, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/862,847

(22) Filed: May 21, 2001

(65) Prior Publication Data

US 2002/0177230 A1 Nov. 28, 2002

Related U.S. Application Data

(60) Provisional application No. 60/206,537, filed on May 21, 2000, and provisional application No. 60/285,320, filed on Apr. 20, 2001.

(51) Int. Cl.[7] ............................ C12P 21/06; C12N 7/00

(52) U.S. Cl. ................. 435/69.1; 435/235.1; 536/23.72

(58) Field of Search ............................ 435/69.1, 235.1; 536/23.72

(56) References Cited

U.S. PATENT DOCUMENTS

| | | | |
|---|---|---|---|
| 5,202,430 A | 4/1993 | Brian et al. .............. | 536/23.72 |
| 5,916,570 A | 6/1999 | Kapil ...................... | 424/222.1 |

OTHER PUBLICATIONS

Almazan et al., "Engineering the largest RNA virus genome as an infectious bacterial artificial chromosome," *PNAS.* vol. 97, No. 10, May 9, 2000, pp. 5516–5521.

Lai, Michael M.C. "The making of infectious viral RNA: No size limit in sight," *PNAS.* vol. 97, No. 10, May 9, 2000, pp. 5025–5027.

Almazan et al., "Engineering the largest RNA virus genome as an infectious bacterial artificial chromosome," *Proceedings of the National Academy of Sciences of USA* 97: 5516–5521 (2000).

Thiel et al., "Infectious RNA transcribed in vitro from a cDNA copy of the human coronavirus genome cloned in vaccinia virus," 82: 1273–1281 (2001).

Yount et al., "Strategy for systematic assembly of large RNA and DNa enomes: Transmissible gastroenteritis virus model," 74: 10600–10611 (2000).

International Search Report of PCT/US01/16564 dated Dec. 7, 2002.

*Primary Examiner*—Hankyel T. Park
(74) *Attorney, Agent, or Firm*—Myers Bigel Sibley & Sajovec, P.A.

(57) ABSTRACT

Full-length, functionally intact genomes or chromosomes are directionally assembled with partial cDNA or DNA subclones of a genome. This approach facilitates the reconstruction of genomes and chromosomes in vitro for reintroduction into a living host, and allows the selected mutagenesis and genetic manipulation of sequences in vitro prior to reassembly into a full length genome molecule for reintroduction into the same or different host. This approach also provides an alternative to recombination-mediated techniques to manipulate the genomes of higher plants and animals as well as bacteria and viruses.

53 Claims, 11 Drawing Sheets

(6 of 11 Drawing Sheet(s) Filed in Color)

Figure 1A. Assembly Strategy of a TGE Infectious Clone.
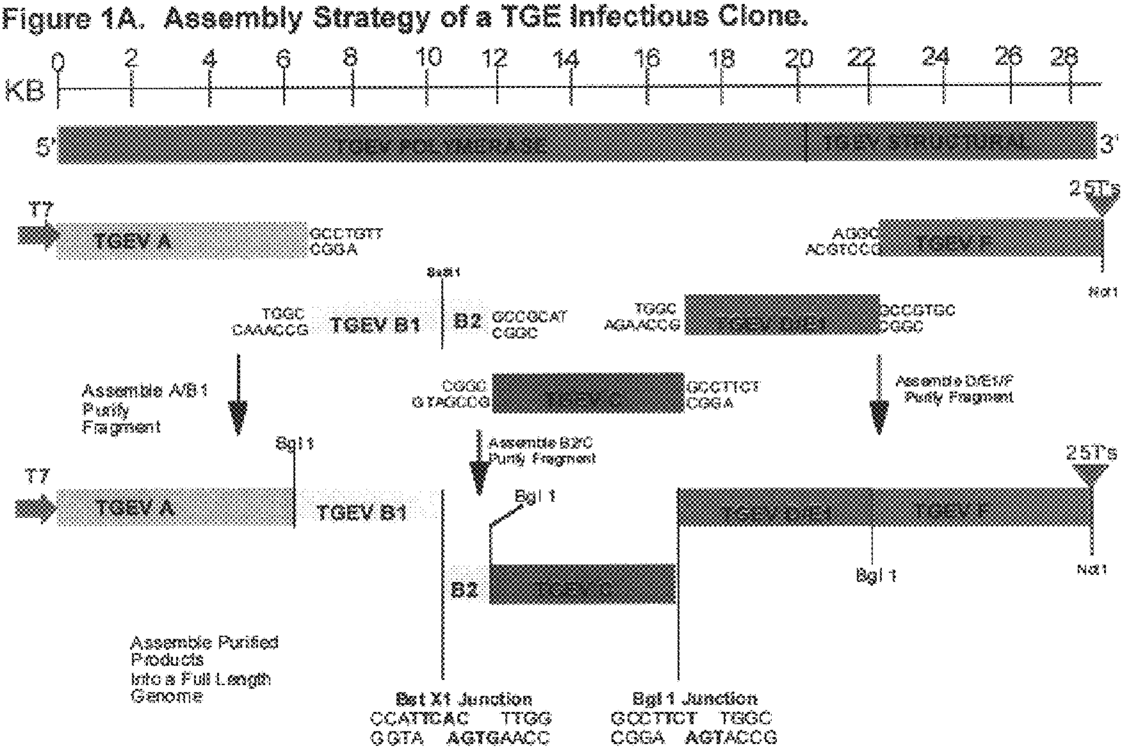

Figure 1B. Cloning the TGE B Fragment.
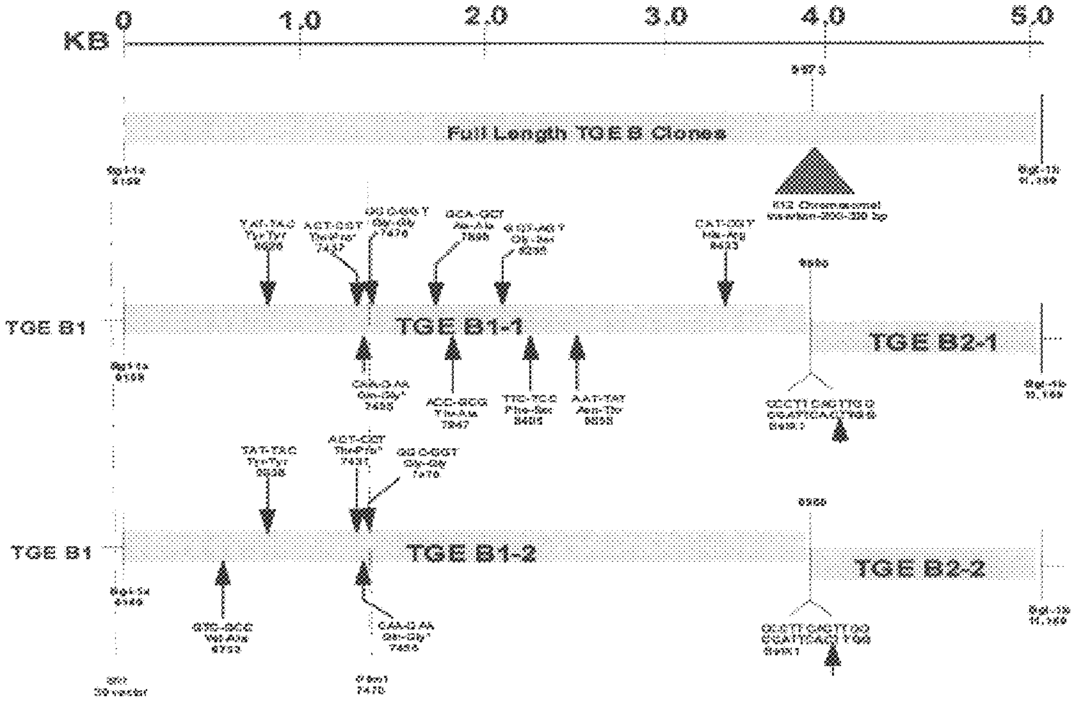

Figure 2. Consensus Sequence of the TGE Infectious clone.
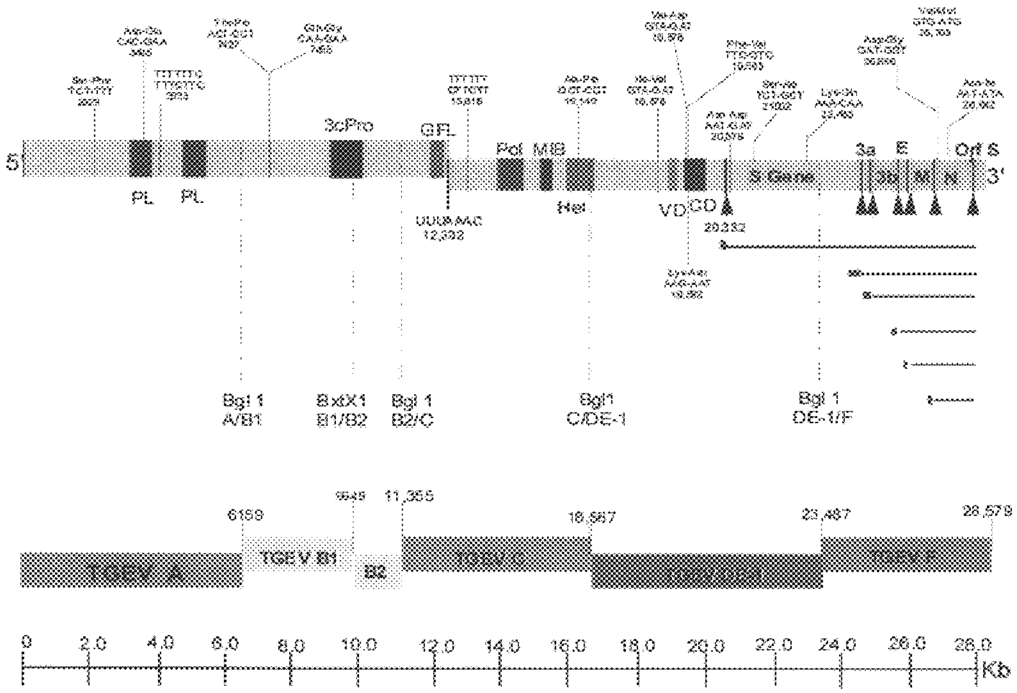

Figure 3. Assembly DATA of Full length infectious clone
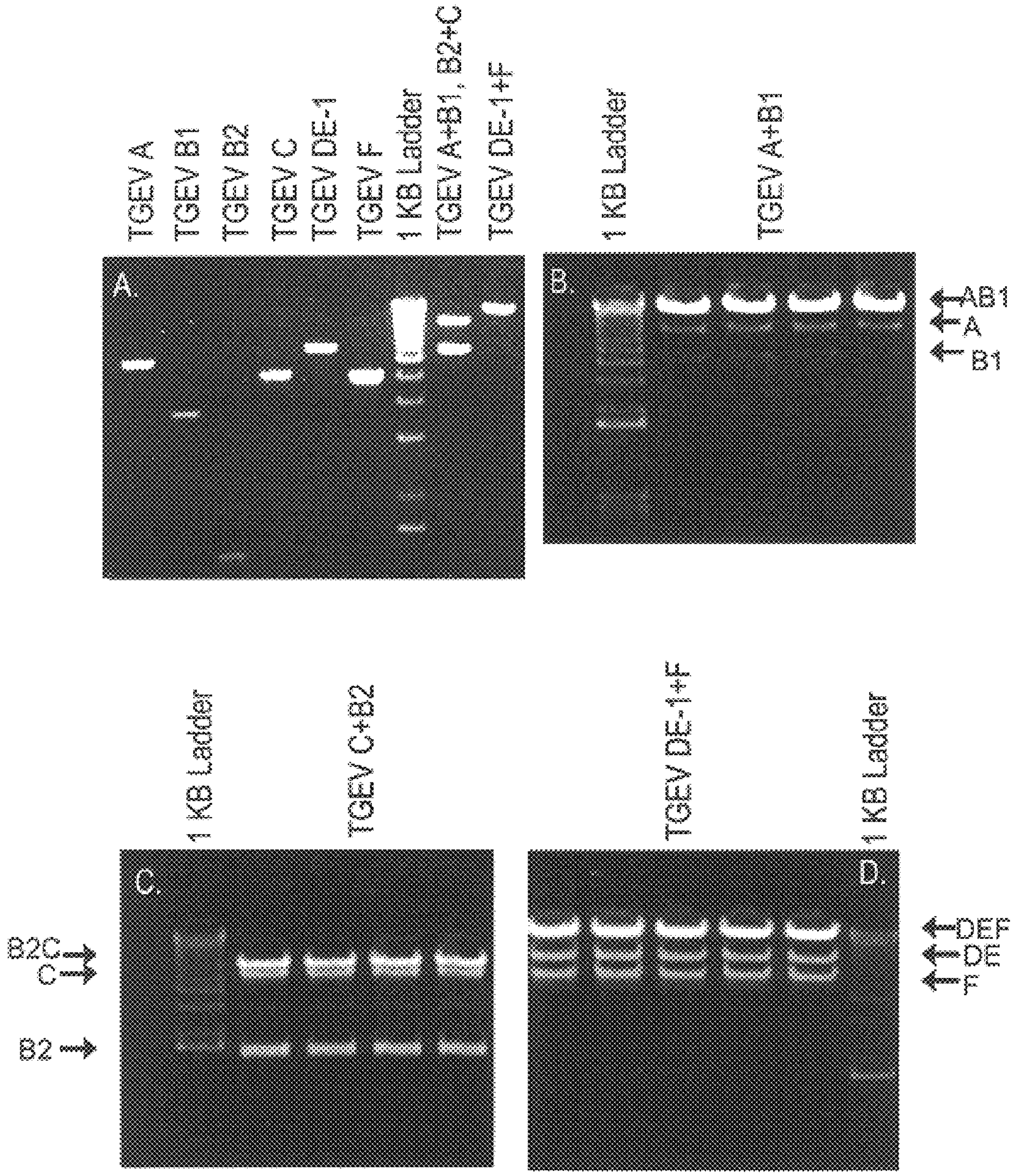

Figure 4. Assembly and In Vitro Transcription of a TGEV Full Length Clones.
Panel A: Assembly of a Full length clone, TGE 1000.
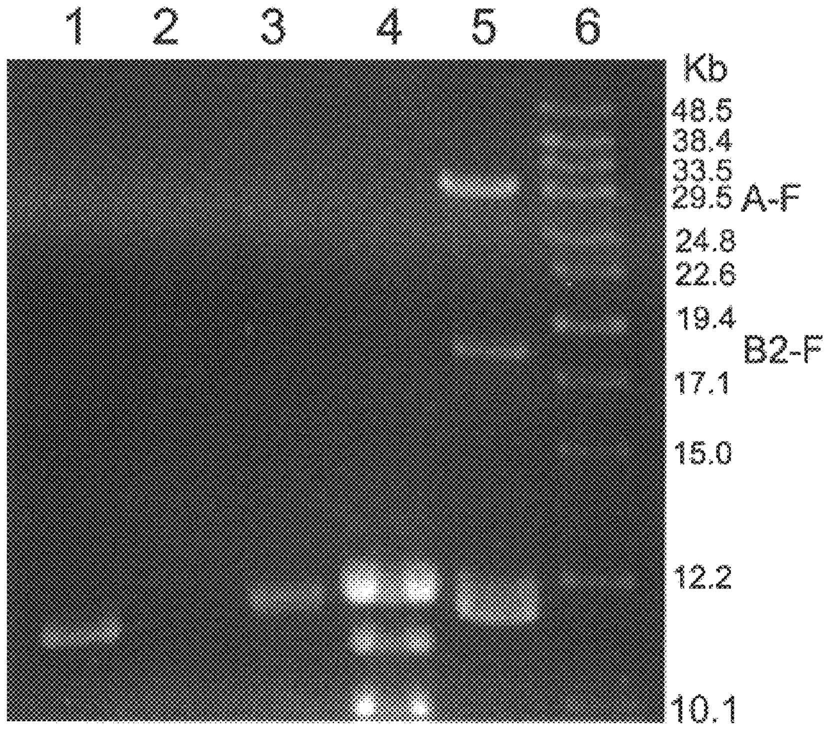

Figure 4B. In vitro Transcripts from the TGE 1000 Construt.
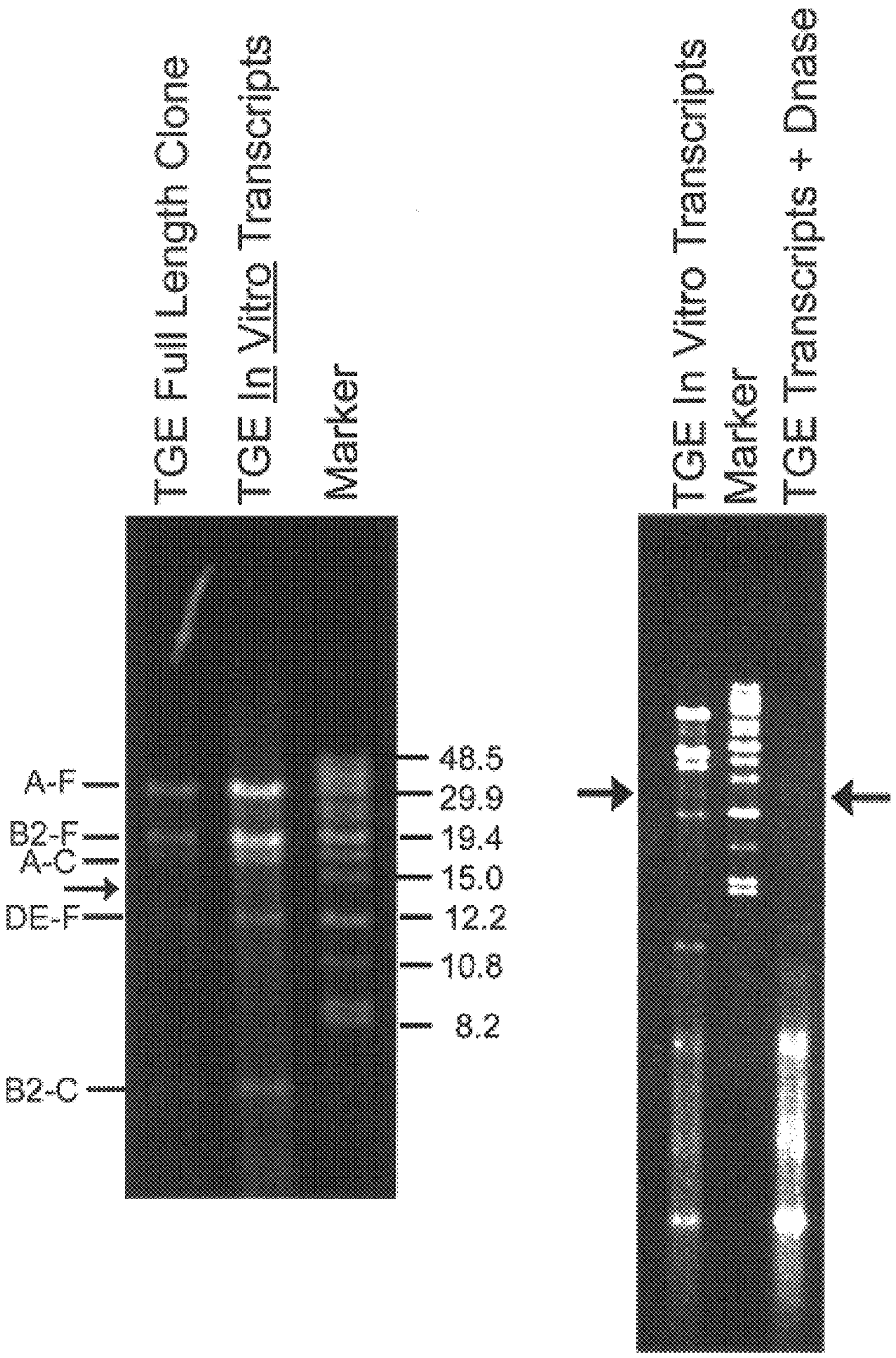

Figure 5. TGE Antigen Expression following Passage in ST cells.
Panel A: uninfected, Panel B: TGE wildtype infection, Panel C: icTGE passage 1, Panel D: icTGE passage 2, Panel E: icTGE passage 3, Panel F: preimmune serum in ST cells.
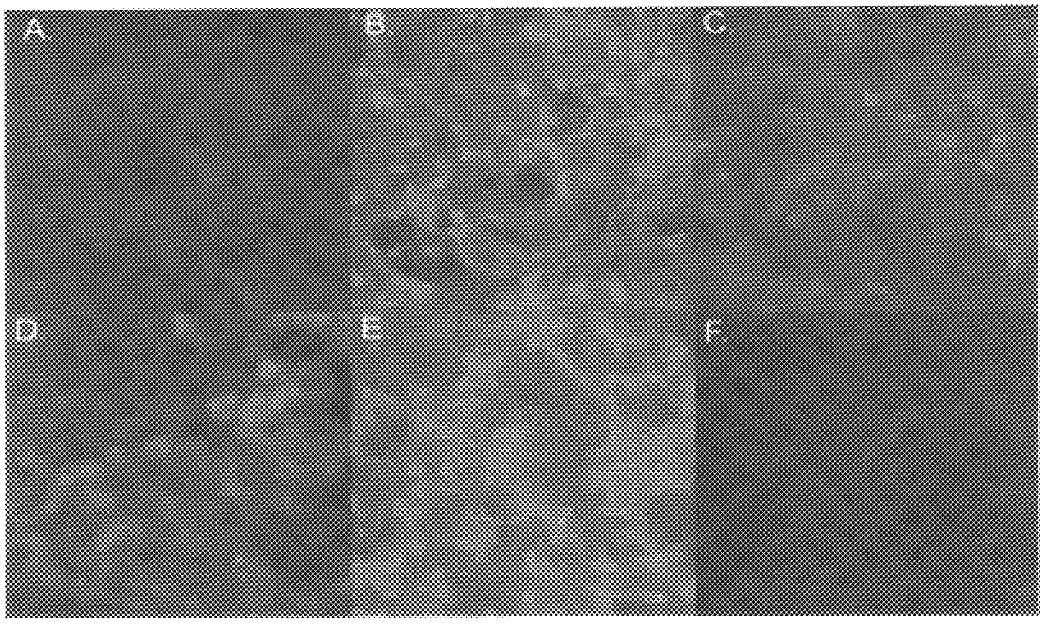

Figure 6. Plaque Morphology of Recovered Viruses.
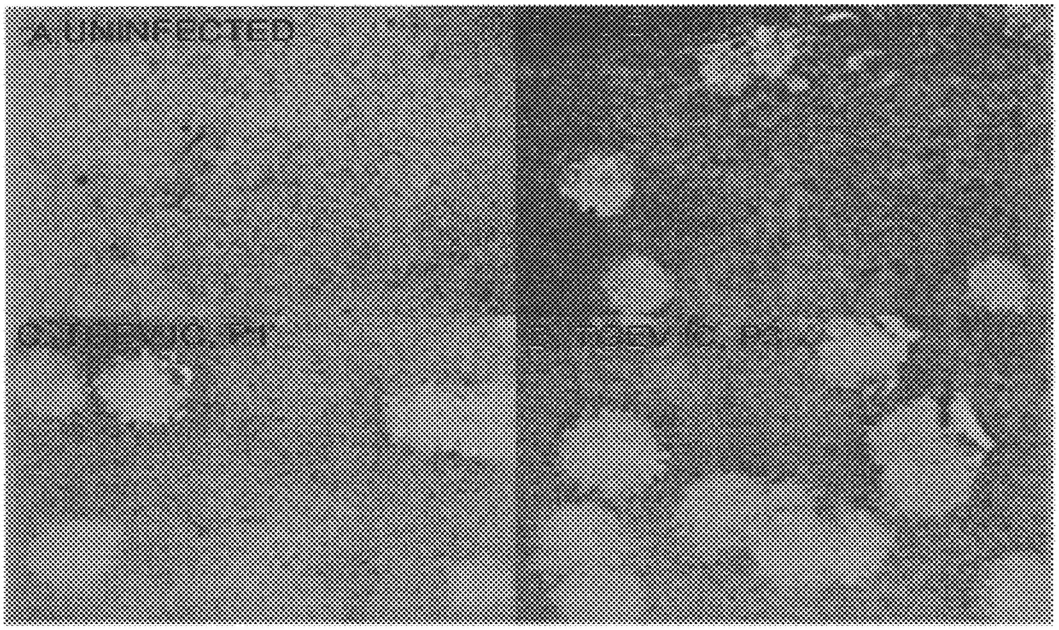

Figure 7. Virions Derived from Infectious Clone form Plaques in ST Cells.
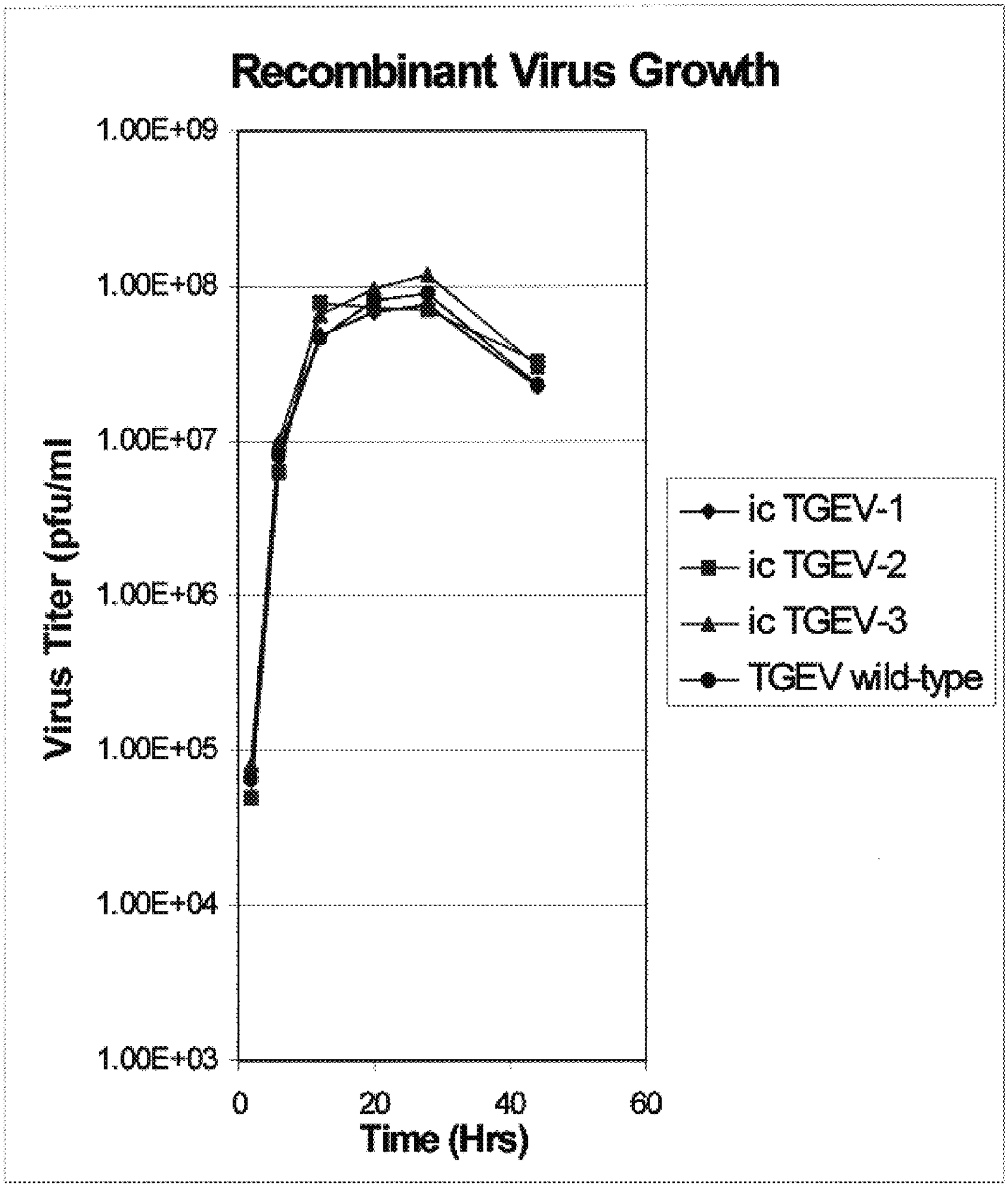

Figure 8. Identification of Marker Mutations in Plaque Purified Recombinant Viruses Derived from the TGE Infectious Clone.
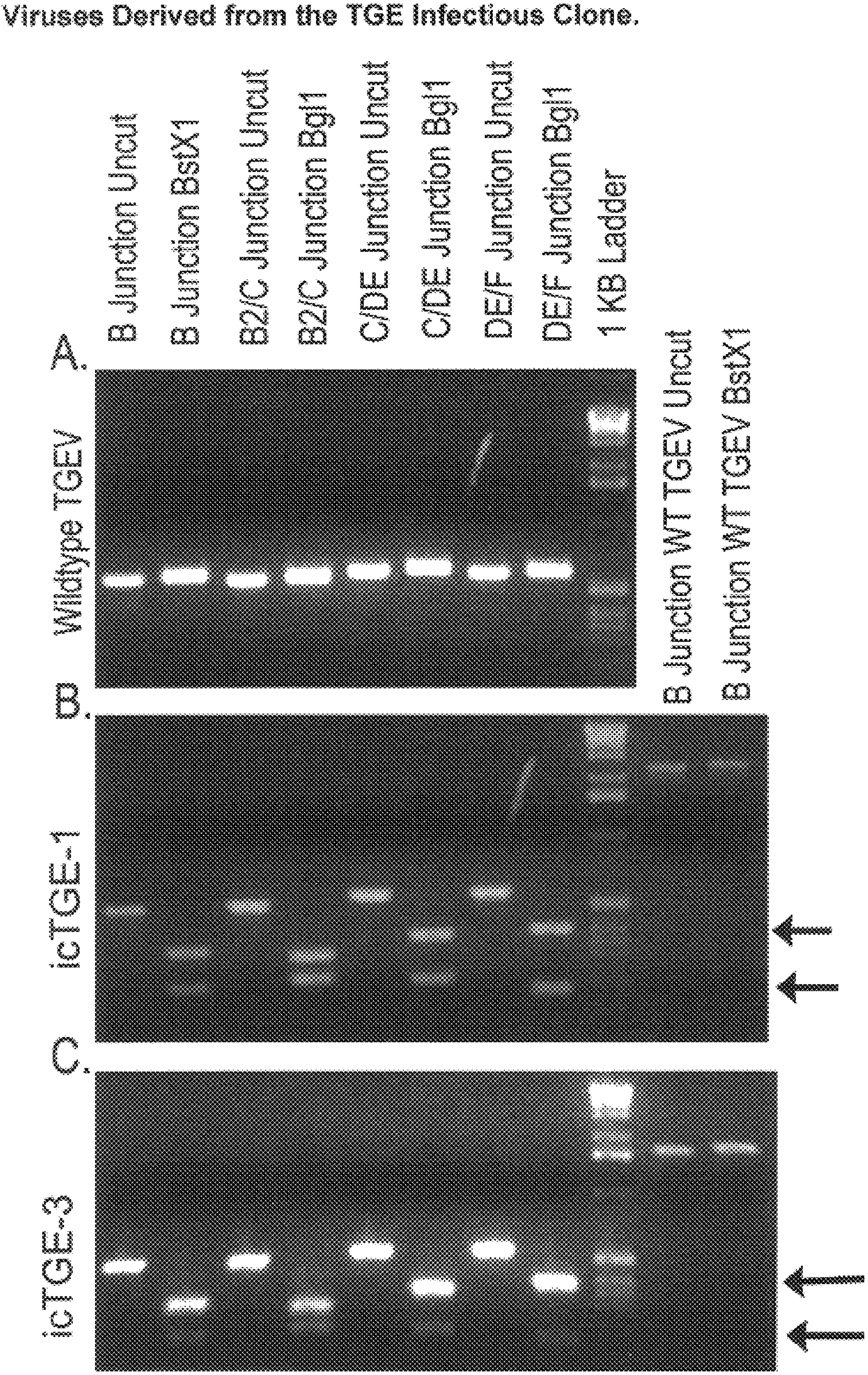

Figure 9. Primer Paris to Assembly the TGE Infectious Clone.

| Primer Designation | Nucleotide*[1] Sequence | Genome Location | Orientation | Purpose |
|---|---|---|---|---|
| 1. TGEV 5' T7 | 5'-**GTCGGCCTC***TTAATACGACTCACTATAGA*-CTTTTAAAGTAAAGTGAG-3' | 1-19 | (+) | Insert T7 Start/Sfi1 TGEV A, 5' End |
| 2. TGEV A 3642 | 5'-TGTTGAAGAAATCAAAGGCCTG-3' | 3642-3621 | (-) | Remove T7 Stop |
| 3. TGEV A 3621 Wt Sequence- | 5'-CAGGCCTTTGATTTCTTCAAC-3' T | 3621-3641 | (+) | Remove T7 Stop Overlap RT-PCR |
| 4. TGEV A 6180 | 5'-CTTGGAGATGTTGAAAATCAGC-3' | 6201-6180 | (-) | TGEV A, 3' End |
| 5. TGEV B1 6134 | 5'-TAAAGTCTGCAGTCTGTGGC-3' | 6115-6134 | (+) | TGEV B1, 5' End |
| 6. TGEV B1 9957 | 5'-TAAT**CCAAGTGAATGGT**GTGTAC-3' | 9957-9935 | (-) | TGEV B1, 3' End Insert BstX1 Site |
| 7. TGEV B2 9939 Wt Sequence- | 5'-ACA**CCATTCACTTGG**ATTAATCC-3' C | 9939-9961 | (+) | TGEV B2, 5' End Insert BstX1 Site |
| 8. TGEV B2 11342 | 5'-GTA**GCCGATGCGGC**TGGAATG-3' | 11,362-11342 | (-) | TGEV B2, 3' End |
| 9. TGEV C 11345 Wt Sequence- | 5'-TCCA**GCCGCATCGGC**TACAAG-3' T A | 11,345-11,365 | (+) | TGEV C, 5' End Insert Bgl1 Site |
| 10. TGEV C 13605 | 5'-GTGCAAAGAAGAAGTGTTTTAATG-3' | 13,628-13,605 | (-) | Remove T7 Stop |
| 11. TGEV C 13609 Wt Sequence- | 5'-AAAACACTTCTTCTTTGCACAGG-3' T T | 13,609-13,631 | (+) | Remove T7 Stop Overlap RT-PCR |
| 12. TGEV C 16,580 | 5'-TGT**GCCAAGAAGGC**CTTGACAAC-3' | 16,585-16,607 | (-) | TGEV C, 3' End |
| 13. TGEV DE 16,585 Wt Sequence- | 5'-CAAG**GCCTTCTTGGC**ACATAATC-3' T A | 16,585-16,607 | (+) | TGEV DE, 5' End Insert Bgl1 Site |
| 14. TGEV DE 3133[+] | 5'-GTCTA**GCCTGCACGGC**TACTGC-3' | 23,496-23,475 | (-) | TGEV DE, 3' End |
| 15. TGEV F 3112[+] Wt Sequence- | 5'-GCAGTA**GCCGTGCAGGC**TAGAC A T | 23,475-23,496 | (+) | TGEV F, 5' End Insert Bgl1 Site |
| 16. TGEV 3' END | 5'NNNNNN**GCGGCCGC**TTTTTTTTTTTTTTTTT-TTTTTTTTTGGTGTATCACTATCAAAAGG-3' | 3' End, Poly A Tail | (-) | TGEV F 3' End Poly A-Tail/Not1 |

*sequences (11,16,30); [1]bolded sequences represent restriction sites; underline represents T7 Start

SEQUENCE LISTING

```
<160> NUMBER OF SEQ ID NOS: 24

<210> SEQ ID NO 1
<211> LENGTH: 11
<212> TYPE: DNA
<213> ORGANISM: Artificial Sequence
<220> FEATURE:
<223> OTHER INFORMATION: BglI recognition sequence.
<221> NAME/KEY: misc_feature
<222> LOCATION: (4)..(8)
<223> OTHER INFORMATION: "n" represents any nucleotide.

<400> SEQUENCE: 1

gccnnnnngg c                                                 11


<210> SEQ ID NO 2
<211> LENGTH: 13
<212> TYPE: DNA
<213> ORGANISM: Artificial Sequence
<220> FEATURE:
<223> OTHER INFORMATION: SfiI recognition sequence.
<221> NAME/KEY: misc_feature
<222> LOCATION: (5)..(9)
<223> OTHER INFORMATION: "n" represents any nucleotide.

<400> SEQUENCE: 2

ggccnnnnng gcc                                               13


<210> SEQ ID NO 3
<211> LENGTH: 47
<212> TYPE: DNA
<213> ORGANISM: Artificial Sequence
<220> FEATURE:
<223> OTHER INFORMATION: Synthetic oligonucleotide primer.

<400> SEQUENCE: 3

tcggcctcga tttaggtgac actatagatg gccaaccagg gacaacg          47


<210> SEQ ID NO 4
<211> LENGTH: 34
<212> TYPE: DNA
<213> ORGANISM: Artificial Sequence
<220> FEATURE:
<223> OTHER INFORMATION: Synthetic oligonucleotide primer.

<400> SEQUENCE: 4

tttttttttt ttttagttcg ttacctcgtc aatc                        34


<210> SEQ ID NO 5
<211> LENGTH: 21
<212> TYPE: DNA
<213> ORGANISM: Artificial Sequence
```

-continued

<220> FEATURE:
<223> OTHER INFORMATION: Synthetic oligonucleotide primer.

<400> SEQUENCE: 5
gcatcgtaag actcaacaag g 21

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide primer.

<400> SEQUENCE: 6
gtcacagcaa gtgagaacca tg 22

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 7
ttgagcgcga agcatcagtg c 21

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide primer.

<400> SEQUENCE: 8
ttccactgcc gaaagcttca cc 22

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 9
gaatgtgcac actaggacct g 21

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide primer.

<400> SEQUENCE: 10
agcaggtggt atgtattgtt cg 22

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 11
cgttgtacag gtggttatga c 21

-continued

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide primer.

<400> SEQUENCE: 12
ctccgcttgt ctggttagag tc 22

<210> SEQ ID NO 13
<211> LENGTH: 11
<212> TYPE: DNA
<213> ORGANISM: Artificial Sequence
<220> FEATURE:
<223> OTHER INFORMATION: Synthetic oligonucleotide.

<400> SEQUENCE: 13
gcctgtttgg c 11

<210> SEQ ID NO 14
<211> LENGTH: 11
<212> TYPE: DNA
<213> ORGANISM: Artificial Sequence
<220> FEATURE:
<223> OTHER INFORMATION: Synthetic oligonucleotide primer.

<400> SEQUENCE: 14
gccgcatcgg c 11

<210> SEQ ID NO 15
<211> LENGTH: 11
<212> TYPE: DNA
<213> ORGANISM: Artificial Sequence
<220> FEATURE:
<223> OTHER INFORMATION: Synthetic oligonucleotide primer.

<400> SEQUENCE: 15
gccttcttgg c 11

<210> SEQ ID NO 16
<211> LENGTH: 11
<212> TYPE: DNA
<213> ORGANISM: Artificial Sequence
<220> FEATURE:
<223> OTHER INFORMATION: Synthetic oligonucleotide primer.

<400> SEQUENCE: 16
gccgtgcagg c 11

<210> SEQ ID NO 17
<211> LENGTH: 11
<212> TYPE: DNA
<213> ORGANISM: Artificial Sequence
<220> FEATURE:
<223> OTHER INFORMATION: AccB71 recognition sequence.
<221> NAME/KEY: misc_feature
<222> LOCATION: (4)..(8)
<223> OTHER INFORMATION: “n” represents any nucleotide.

<400> SEQUENCE: 17
ccannnnntg g 11

<210> SEQ ID NO 18
<211> LENGTH: 10
<212> TYPE: DNA

-continued

<213> ORGANISM: Artificial Sequence
<220> FEATURE:
<223> OTHER INFORMATION: Alw261 recognition sequence.
<221> NAME/KEY: misc_feature
<222> LOCATION: (6)..(10)
<223> OTHER INFORMATION: "n" represents any nucleotide.

<400> SEQUENCE: 18 gtctcnnnnn 10

<210> SEQ ID NO 19
<211> LENGTH: 12
<212> TYPE: DNA
<213> ORGANISM: Artificial Sequence
<220> FEATURE:
<223> OTHER INFORMATION: BstXI recognition sequence.
<221> NAME/KEY: misc_feature
<222> LOCATION: (4)..(9)
<223> OTHER INFORMATION: "n" represents any nucleotide.

<400> SEQUENCE: 19
ccannnnnnt gg 12

<210> SEQ ID NO 20
<211> LENGTH: 11
<212> TYPE: DNA
<213> ORGANISM: Artificial Sequence
<220> FEATURE:
<223> OTHER INFORMATION: SapI recognition sequence.
<221> NAME/KEY: misc_feature
<222> LOCATION: (8)..(11)
<223> OTHER INFORMATION: "n" represents any nucleotide.

<400> SEQUENCE: 20
gctcttcnnn n 11

<210> SEQ ID NO 21
<211> LENGTH: 11
<212> TYPE: DNA
<213> ORGANISM: Artificial Sequence
<220> FEATURE:
<223> OTHER INFORMATION: BbsI recognition sequence.
<221> NAME/KEY: misc_feature
<222> LOCATION: (7)..(11)
<223> OTHER INFORMATION: "n" represents any nucleotide.

<400> SEQUENCE: 21
gaagacnnnn n 11

<210> SEQ ID NO 22
<211> LENGTH: 11
<212> TYPE: DNA
<213> ORGANISM: Artificial Sequence
<220> FEATURE:
<223> OTHER INFORMATION: PflmI recognition sequence.
<221> NAME/KEY: misc_feature
<222> LOCATION: (4)..(8)
<223> OTHER INFORMATION: "n" represents any nucleotide.

<400> SEQUENCE: 22
ccannnnntg g 11

<210> SEQ ID NO 23
<211> LENGTH: 17
<212> TYPE: DNA
<213> ORGANISM: Artificial Sequence
<220> FEATURE:
<223> OTHER INFORMATION: BbvI recognition sequence.
<221> NAME/KEY: misc_feature -continued

```
<222> LOCATION: (6)..(17)
<223> OTHER INFORMATION: "n" represents any nucleotide.

<400> SEQUENCE: 23

gcagcnnnnn nnnnnnn                                                    17


<210> SEQ ID NO 24
<211> LENGTH: 12
<212> TYPE: DNA
<213> ORGANISM: Artificial Sequence
<220> FEATURE:
<223> OTHER INFORMATION: Synthetic oligonucleotide.

<400> SEQUENCE: 24

ccattcactt gg                                                         12
```

DIRECTIONAL ASSEMBLY OF LARGE VIRAL GENOMES AND CHROMOSOMES

RELATED APPLICATIONS

This application claims the benefit of U.S. Provisional Application No. 60/206,537, filed May 21, 2000, and U.S. Provisional Application No. 60/285,320, filed Apr. 20, 2001, both of which are incorporated herein by reference in their entirety.

STATEMENT OF FEDERAL SUPPORT

The present invention was made with government support under grant number AI23946-08 from the National Institutes of Health. The United States government has certain rights to this invention.

FIELD OF THE INVENTION

This invention relates to the directional assembly of large genomes, and more specifically, to the directional assembly of large viral genomes.

BACKGROUND OF THE INVENTION

The genomes of viruses, bacteria, plants and other organisms (including humans) are being systematically cloned and sequenced. Methods are needed to directionally assemble smaller DNA subclones into full-length, functionally intact genomes or chromosomes of these organisms. Such methods could allow for the precise genetic manipulation of individual chromosomes in whole plants and animals and the construction of artificial chromosomes for gene therapy. Conventional approaches have generally not been successful because of the large size of the target nucleic acid and the inability to systematically assemble individual DNA clones into a full-length genome.

Presently known methods for genetically manipulating the genomes of many viruses, plants, animals, and bacteria generally use recombination or transduction methods to introduce foreign sequences or alter genes in the genomes of organisms. These methods can be problematic depending on the payload sequences being introduced and the biology of the organism. In addition, multiple genetic manipulations/recombination events may be required to construct the appropriate genotype.

Molecular genetic analysis of the structure and function of RNA virus genomes has been profoundly advanced by the availability of full-length cDNA clones, the source of infectious RNA transcripts that replicate efficiently when introduced into permissive cell lines. See P. Ahlquist, et al., *Proc. Natl. Acad. Sci.* USA 81, 7066–7070 (1984); J. C. Boyer et al., *Virology* 198, 415–426 (1994). Recombinant DNA technology has allowed the isolation of infectious cDNA clones from a variety of positive-stranded RNA viruses including picornaviruses, caliciviruses, alphaviruses, flaviviruses and arterioviruses, whose RNA genomes range in size from approximately 7–15 kb in length. See Agapov, E. V. et al., *Proc. Natl. Acad. Sci.* USA 95, 12989–12994 (1998); Davis, N. L., et al, *Virology* 171, 189–204(1989); Racaniello, V. R. et al., *Science* 214, 916–919(1981); Rice, C. M., et al., *New Biol.* 1, 285–296(1989); Rice, C. M., et al, *J. Virology* 61, 3809–3819 (1987); Sosnovtsev, S. et al., *Virology* 210, 383–390 (1995); Sumyoshi, H., et al., *J. Virol.* 66, 5425–5431 (1992); Van Dinten, L. C et al., *Proc. Natl. Acad. Sci.* USA 94, 991–996 (1997).

The order Nidovirales (the Nidoviruses) includes mammalian, positive polarity, single-stranded RNA viruses in the arteriviruses and coronavirus families. Cavanagh, D., et al., *Arch. Virol.* 128, 395–396 (1993); De Vries, A. A. F., et al., *Semin. Virol.* 8, 33–47 (1997). Coronaviridae (the coronavirus family) includes the coronavirus and torovirus genuses. See Cavanagh et al., supra; Snijder, E. J. et al., *J. Gen. Virol.* 74, 2305–2316 (1993). Despite significant size differences (13–32 Kb), the polycistronic genome organization and regulation of gene expression from a nested set of subgenomic mRNAs are similar for all members of the order. See De Vries et al., supra and Snijder et al., supra.

Coronaviridae contain a linear, single-stranded positive polarity RNA genome of about 27–32,000 nucleotides in length. As such, the family contains the largest known RNA viral genomes. Lai, M. M. C et al., *Adv. Virus Res.* 48, 1–100 (1997); Siddell, S. G. *The Coronaviridae, an introduction, in The Coronaviridae* (Plenum Press, New York. Pgs 1–10 (1995)). Transmissible gastroenteritis virus (TGE), a group I coronavirus, contains an approximately 28.5 Kb genomic RNA that is packaged into a helical nucleocapsid structure and is surrounded by an envelope that contains three virus specific glycoprotein spikes, including the S glycoprotein, membrane glycoprotein (M), and a small envelope glycoprotein (E). See Eleouet, J. F., et al, *Virology* 206, 817–822 (1995); Enjuanes, L. et al., *Molecular basis of transmissible gastroenteritis coronavirus (TGE) epidemiology, in The Coronaviridae* (S. G. Siddell, ed., pp 337–376. Plenum Press, New York (1995)); Rasschaert, D. et al, *J. Gen. Virol.* 68, 1883–1890 (1987); Risco, C., et al., *J. Virol.* 70, 4773–4777 (1996).

The TGE genome is polycistronic and encodes nine large open reading frames (ORFs) which are expressed from full length or subgenomic length mRNAs during infection. Sethna, P. B., et al., *J. Virol.* 65, 320–325 (1991); Sethna, P. B., et al, *Proc. Natl. Acad. Sci.* USA 86, 5626–5630 (1989). The 5'-most 20 Kb (approximately) encodes the RNA replicase genes that are encoded in two large ORF's designated 1a and 1b, the latter of which is expressed by ribosomal frameshifting. Eleouet, J. F et al., supra. ORF1*a* encodes at least two viral proteases and several other nonstructural proteins, while ORF1*b* contains polymerase, helicase and metal binding motifs typical of an RNA polymerase. See Eleouet, et al., supra, Gorbalenya, A. E., et al,. Nucleic Acids Res. 17, 4847–4861 (1989). In the 3'-most 9 Kb (approximately) of the TGE genome, each of the downstream ORFs is preceded by a highly conserved intergenic sequence element, which directs the synthesis of each of the six or seven subgenomic RNAs. See Chen, C. M., et al., *Virus Res.* 38, 83–89 (1997); Eleouet et al., supra; Enjuanes, et al., supra; Tung, F. Y. T., et al, *Virology* 186, 676–683 (1992). These subgenomic mRNAs are arranged in a nested set structure from the 3' end of the genome and contain a leader RNA sequence derived from the 5' end of the genome. See Lai, M. M. C. et al., supra; McGoldrick, A., et al., Arch Virol. 4, 763–770 (1999); Sethna (1991), supra; Sethna (1989), supra. In addition to the viral mRNAs, full length and subgenomic length negative strand RNAs are implicated in mRNA synthesis. Almazan, F., et al., *Proc. Natl. Acad. Sci.* USA 97, 5516–5521 (2000). Another unique feature of coronavirus replication is the high RNA recombination frequencies associated with infection. Baric, R. S., et al., Virology 177, 646–656 (1990); Kuo, L., et al., *J. Virol.* 74, 1393–1406 (2000); Lai et al., supra.

The large size of the coronavirus genome, coupled with the inability to clone portions of the polymerase gene in microbial vectors, has hampered the ability to perform precise manipulations and reverse genetics in Coronaviridae. Recently, a full length cDNA clone of TGE was assembled in bacterial artificial chromosomes (BAC) vectors. See Almazan, F., et al., supra. However, the assembly of large RNA and DNA genomes using these BAC vector methods remains problematic.

The family of coronaviruses includes viruses that are responsible for severe economic losses in the swine, cattle and poultry industries and cause about 30% of the common colds in humans. In children and infants, human coronaviruses may cause more serious lower respiratory tract infections including bronchitis, bronchiolitis and pneumonia. Transmissible gastroenteritis virus (TGE) cause acute diarrhea in piglets often resulting in mortality rates approaching 100% and an estimated annual loss of greater than 30 million dollars per year in the US alone. Infectious bronchitis virus (IBV) cause severe lower respiratory tract infection in poultry resulting in approximately $20,000,000 losses each year. Since presently known TGE and IBV vaccines have not been effective at reducing the severity of disease, new methods are needed to efficiently engineer recombinant TGE viral vaccines and use these viruses to deliver other antigens from highly virulent pathogenic microorganisms of swine.

The unique replication strategy of coronaviruses makes them attractive candidate vectors to express multiple foreign genes. TGE vectors engineered to express multiple recombinant proteins or foreign antigens from highly pathogenic microorganisms may be effective at reducing overall economic losses from infectious agents in, for example, swine.

SUMMARY OF THE INVENTION

The present invention relates to a simple, systematic method for assembling functional full-length genomes of large RNA and DNA viruses. The invention is exemplified by, although not limited to, the assembly of full-length, functional coronavirus genomes. The present inventors have successfully assembled a full length infectious clone of transmissible gastroenteritis virus (TGE). Using a novel approach, six adjoining cDNA subclones that span the entire TGE genome were isolated. Each clone was engineered with unique flanking interconnecting junctions which dictate a precise, systematic assembly with only the correct adjacent cDNA subclones, resulting in an intact TGE cDNA construct of about approximately 28.5 Kb in length. Transcripts derived from the full-length TGE construct were found to be infectious, and progeny virions were serially passaged in permissive host cells. Viral antigen and subgenomic mRNA synthesis were evident during infection and throughout passage. Plaque-purified virus derived from the infectious construct was found to replicate efficiently in permissive host cells. The recombinant viruses were sequenced across the unique interconnecting junctions, conclusively demonstrating the unique marker mutations and restriction sites that were engineered into the component clones. Among other advantages, full-length infectious clones of TGE permit the precise genetic modification of the coronavirus genome.

Accordingly, a first aspect of the present invention is a method of assembling a recombinant viral genome by obtaining a set of subclones of the viral genome, wherein the termini of each subclones is a restriction site, and then ligating the subclones to form a recombinant viral genome. The genome is preferably a full-length viral genome that has the same activity (function) as the natural genome, and more preferably is an infectious viral genome (i.e., is able to infect permissive cells). In certain embodiments, the subclones comprise mutations (i.e., have sequences that are different from the wild type genome). In other embodiments, the assembled genome further comprises a heterologous nucleic acid. In a preferred embodiment, the viral genome is a coronavirus genome. Recombinant viral genomes produced by the present invention are an additional aspect of the present invention. Methods of infecting cells with genomes of the present invention are yet another aspect of the present invention. In preferred embodiments of these methods, the genomes are vectors that express heterologous nucleic acid in the cell.

The foregoing and other aspects of the present invention are explained in detail in the specification set forth below.

BRIEF DESCRIPTION OF THE DRAWINGS

The file of this patent contains at least one drawing executed in color. Copies of this patent with color drawings are provided to the Patent and Trademark Office with payment of the necessary fee.

FIGS. 1A, 1B and 1C are graphical illustrations of a strategy for directionally assembling a transmissible gastroenteritis (TGE) virus infectious clone.

FIG. 1A graphically illustrates that the TGE genome is a linear, positive polarity RNA of about 29,000 nucleotides in length. Using RT-PCR and unique oligonucleotide primer mutagenesis, five clones spanning the entire TGE genome were isolated using standard recombinant DNA techniques. Unique Bgl sites were inserted at the junctions between each clone, a unique T7 start site was inserted at the 5' end of clone A, and a 25 nucleotide T-Tail and downstream Not1 site inserted at the 3' end of clone F. The approximate location of each site is shown.

FIG. 1B illustrates a scheme for the cloning of TGE B amplicons. It was noted that several B clones (TGE B1, B3) contained large insertions at nucleotide 9973 in the TGE genome. Other TGE B clones had deletions across these sequences. The B fragment was bisected by inserting a BstX1 site at position 9950 and cloning two separate clones designated TGE B1-1, 2 and TGE B2-1, 2. Sequence variation in these clones is shown. Isolating a Sfi1/Pflm1 fragment from B1-1 and inserting this into the TGE B1-2 clone created a wildtype B1 fragment.

FIG. 1C is a graphical illustration of the location of TGE subclones in the TGE genome. The TGE subclones used to synthesize a TGE full-length clone are shown in relationship to important motifs, cis-acting sequences or genes in the TGE genome. The relative location of the different TGE motifs was estimated based on the work of Eleout et al. (1995), supra.

FIG. 2 is a graphical illustration of the sequence and chromosomal location of TGE subclones. The consensus amino acid changes that differ from the published sequence are shown in each of the final clones used to assemble a full-length TGE clone. Consensus estimates were based on sequencing three to six independent clones. Abbreviations: PL=papain-like protease, 3cPro=polio 3c-like protease, GFL=growth factor-like domain, Pol=polymerase motif, MIB=metal binding motif, Hel=helicase motif, VD=variable domain, CD=conserved domain, ↑=intergenic starts.

FIG. 3 is a photographic illustration of the assembly of the TGE full length clone. Various TGE plasmid DNA's were digested with Bgl1, BstX1 or Not1, and the appropriate sized products isolated from agarose gels as described in the Examples. These products are shown in Panel 3A. The TGE A and B1A fragments, TGE B2A and C3-2 fragments, or TGE DE-1 and F fragments were ligated at 16° C. overnight in separate reactions. Appropriate-sized products were isolated from agarose gels. Panel B: A+B1, Panel C: B2+C, Panel D: DE-1+F. Following purification from agarose gels, the purified products are also shown in Panel A as well.

FIG. 4 is a photographic illustration of in vitro transcription from full length TGE constructs. The purified products from FIG. 3 were mixed and ligated overnight at 16° C. in the presence of T4 DNA ligase. The products were phenol/chloroform-chloroform extracted and precipitated under ethanol and a portion separated in 0.5% agarose gels (Panel A). Lane 1: A/B1 fragment, Lane 2: B2/C (has run off the gel), Lane 3: DE/F fragment, Lane 4: 1 Kb ladder, Lane 5: Ligation Products of A/B1, B2/C, DE/F fragments, Lane 6: high molecular weight marker. Panel B illustrates in vitro transcripts synthesized from the full-length TGE clone. One sixth of the TGE 1000 construct was transcribed in vitro with T7 RNA polymerase and $1/10^{th}$ of the in vitro reaction compared to the untranscribed TGE construct alone. Transcripts were also treated with DNase I.

FIG. 5 is a photographic illustration of transcripts from TGE 1000. Infectious cultures of BHK cells were transfected with TGE+N gene transcripts and seeded into cultures containing $1\times10^6$ permissive ST cells. Virus progeny were harvested at three days post-infection and passaged every 2 days in swine ST cells for three passages. Panel A: uninfected ST cells, Panel B: TGE Wildtype Virus, Panel C: icTGE-pass1, Panel D: icTGE-pass2, Panel E: icTGE-pass3, Panel D: preimmune serum in ST cells. Arrows point to the putative full-length transcript.

FIG. 6 is a photographic illustration of plaque morphology of icTGE Viruses. Cultures of ST cells were infected with wildtype TGE, icTGE-1 and icTGE-3. Cells were stained with neutral red at 48 hrs post-infection and images digitized and prepared using Adobe PhotoShop® 5.5.

FIG. 7 is a graphical illustration of growth curves of plaque purified TGE infectious clone viruses. Plaque purified wildtype TGE and recombinant TGE viruses (icTGE-1, icTGE-2, and icTGE-3) derived from the infectious clone were inoculated into ST cells at a MOI of 5 for one hour at room temperature. The virus was removed and the cultures incubated in complete medium at 37° C.

FIG. 8 photographically illustrates that marker mutations are present in virus derived from the infectious clone. Cultures of ST cells were infected with wildtype TGE or plaque purified TGE isolates derived from the infectious clone. RT-PCR was performed using primer pairs that asymmetrically flank each of the unique Bgl1/BstX1 junctions inserted into the infectious clone. Panel A: wild type TGE; Panel B: icTGE-1 (passage 1); Panel C: icTGE-3 (passage 3). In panels B and C, a larger, approximately 2.5 Kb wild type TGE amplicon spanning the B1/B2 junction is also treated with BstX1 as a control.

FIG. 9 is a table of primer pairs used to assemble a TGE infectious clone as set forth in the Examples.

DETAILED DESCRIPTION OF THE PREFERRED EMBODIMENTS

The present invention will now be described more fully hereinafter with reference to the accompanying figures and specifications, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Nucleotide sequences are presented herein by single strand only, in the 5' to 3' direction, from left to right. Nucleotides and amino acids are represented herein in the manner recommended by the IUPAC-IUB Biochemical Nomenclature Commission, in accordance with 37 C.F.R. §1.822 and established usage. See, e.g., Patent In User Manual, 99–102 (November 1990) (U.S. Patent and Trademark Office).

Except as otherwise indicated, standard methods may be used for the production of cloned genes, expression cassettes, vectors (e.g., plasmids), proteins and protein fragments according to the present invention. Such techniques are known to those skilled in the art. See e.g., J. Sambrook et al., *Molecular Cloning: A Laboratory Manual Second Edition* (Cold Spring Harbor Laboratory, Cold Spring Harbor, N.Y., 1989), and F. M. Ausubel et al., *Current Protocols In Molecular Biology* (Green Publishing Associates, Inc. and Wiley-Interscience, New York, 1991).

As used herein, a nucleic acid molecule may be RNA (the term "RNA" encompassing all ribonucleic acids, including but not limited to pre-mRNA, mRNA, rRNA, hnRNA, snRNA and tRNA); DNA; peptide nucleic acid (PNA, as described in, e.g., U.S. Pat. No. 5,539,082 to Nielsen et al., and U.S. Pat. No. 5,821,060 to Arlinghaus et al.); and the analogs and modified forms thereof. Nucleic acid molecules of the present invention may be linear or circular, an entire gene or a fragment thereof, full-length or fragmented/digested, "chimeric" in the sense of comprising more than one kind of nucleic acid, and may be single-stranded or double-stranded. Nucleic acid from any source may be used in the present invention; that is, nucleic acids of the present invention include but are not limited to genomic nucleic acid, synthetic nucleic acid, nucleic acid obtained from a plasmid, cDNA, recombinant nucleic acid, and nucleic acid that has been modified by known chemical methods, as further described herein.

Nucleic acids of the present invention may be obtained from any organism, including but not limited to bacteria, viruses, fungi, plants and animals, with viral nucleic acid being preferred. If desired, the nucleic acid may be amplified according to any of the known nucleic acid amplification methods that are well-known in the art (e.g., PCR, RT-PCR, QC-PCR, SDA, and the like). Nucleic acids of the present invention may be, and preferably are, purified according to methods known in the art. In general, nucleic acid molecules of the present invention are nucleic acid molecules that are suspected of containing at least one mutation, the determination of the presence of the mutation being desired by the practitioner; or for which the amount or concentration is useful to be determined; or that undergo a conformational change.

A mutation of the present invention may be a deletion mutation, an addition (insertion) mutation, or a point mutation, as these terms are understood in the art. Mutations that can be identified by the methods of the present invention include, but are not limited to, those mutations in sequences that regulate transcription or translation of a gene, nonsense mutations, splice site alterations, and translocations.

A "recombinant virus" is a virus that has been genetically altered, e.g., by the addition or insertion of a heterologous nucleic acid construct into the viral genome, or by the creation of a mutation in the viral genome, or that has been assembled from a series of subclones (i.e., subsequences of the complete genome). A recombinant virus may be a viral particle (e.g., a genomic RNA in a viral capsid), or a nucleic acid or plurality of nucleic acids encoding the complete recombinant virus.

The term "heterologous" as it relates to nucleic acid sequences such as coding sequences and control sequences, denotes sequences that are not normally joined together, and/or are not normally associated with a particular cell or virus infection. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct, which is not normally present in the cell, would be considered heterologous for purposes of this invention. Allelic variation or naturally-occurring mutational events do not give rise to heterologous DNA, as used herein.

The term "infecting" or "transfecting" is used to refer to the uptake of foreign DNA or RNA by a cell, and a cell has been "infected" or "transfected" when exogenous DNA or RNA has been introduced inside the cell membrane. A number of infection or transfection techniques are generally known in the art. See, e.g., Graham et al. (1973) *Virology,* 52:456; Sambrook et al. supra; Davis et al. (1986) *Basic Methods in Molecular Biology* (Elsevier Press); and Chu et al. (1981) *Gene* 13,197. Such techniques can be used to introduce one or more exogenous DNA or RNA moieties, such as a nucleotide integration vector and other nucleic acid molecules, into suitable host cells.

"Non-permissive" cells used in the methods of the present invention are cells which, upon transfection with a viral RNA transcript or a DNA construct (i.e., a construct that encodes and expresses the viral RNA), are not capable of producing viral particles. Virus "permissive" cells used in the methods of the present invention are cells which, upon transfection with a viral RNA transcript or a DNA construct, are capable of producing viral particles or efficiently replicating the virus RNA.

The term "host cell" denotes, for example, microorganisms, yeast cells, insect cells, and mammalian cells, that can be, or have been, used as recipients of an viral construct, an viral vector plasmid, an accessory function vector, or other transfer DNA or RNA. The term includes the progeny of the original cell which has been transfected. Thus, a "host cell" as used herein generally refers to a cell which has been transfected with an exogenous DNA or RNA sequence. It is understood that the progeny of a single parental cell may not necessarily be completely identical in morphology or in genomic or total DNA complement as the original parent, due to natural, accidental, or deliberate mutation. Mammalian host cells are currently preferred.

The term "virus" as used herein refers to all types of viruses, including naked viruses and enveloped viruses. Examples include, but are not limited to, human papillomaviruses, lentiviruses such as human immunodeficiency virus and SIV, enteroviruses (e.g., poliovirus, hepatitis A virus), hepatitis C virus, influenza virus, herpesvirus, nidoviruses (e.g., coronaviruses, infectious bronchitis virus (IBV), transmissible gastroenteritis (TGE) virus, equine arteritis virus, and berne virus), mononegavirales (e.g., measles, rabies, ebola), alphaviruses, calciviruses, rotaviruses toroviruses, filoviruses (e.g., Ebola, Marburg) and flaviviruses (e.g., yellow fever virus, dengue virus). In preferred embodiments of the invention, the virus is a nidovirus; more preferably, a coronavirus, and even more preferably, a TGE virus).

Although the Applicant does not wish to be bound to any particular theory of the invention, certain embodiments of the present invention are based on the fact that conventional restriction enzymes, such as Pst1 and EcoR1, leave "sticky" (i.e., non-blunt) ends that assemble with similarly cut DNA fragments in the presence of DNA ligase. The most rare restriction enzymes (e.g., Not1, etc.) recognize an eight-nucleotide palindrome sequence and cleave DNA every 65,000 bp, on average. Because this class of restriction enzymes leaves compatible ends that randomly concatomerize or reassemble with other DNA molecules having a similar compatible end, they rarely are appropriate choices for assembling large intact genomes or chromosomes. However, a second subclass of restriction enzymes (i.e. Bgl1, BstX1) also recognizes palindrome sequences, but leaves random sticky ends of one to four nucleotides in length that are not complementary to most other sticky ends generated with the same enzyme at other sites in the DNA. For example, BglI recognizes the palindrome sequence GCCNNNN↓NGGC (SEQ ID NO:1), and is predicted to cleave the DNA every approximately 4096 base pairs. Because a three-nucleotide variable overhang is generated following cleavage, 64 different variable ends will be generated, which assemble only with the appropriate three nucleotide complementary overhang generated at an identical Bgl1 site (FIG. 9). Consequently, identical Bgl1 sites are repeated about every approximately 261,344 base pairs in a given stretch of DNA. If the DNA pieces are sorted using recursive techniques, approximately $2^{64}$ fragments of either approximately 4,000, or approximately 64,000 bp (average size) in length can be systematically assembled with different Bgl1 or Sfi1 (GGCCNNNN↓NGGCC; SEQ ID NO:2) ends, respectively.

In view of the foregoing, embodiments of the present invention thus relate to methods of preparing sequential series of smaller DNA subclones (i.e., subsequences of the entire genome) that are flanked by unique restriction sites (e.g., Bgl1 junctions) that could be systematically and precisely reassembled into an intact full length infectious viral genome (e.g., a TGE cDNA). In one embodiment of the invention, a full length infectious construct of a coronavirus is assembled. In a preferred embodiment, a full length infectious construct of the TGE genome is assembled. The number of subclones used to assemble the full length genome will vary according to the size of the genome, the stability of the genome, the biology of the genome, etc. In general, the number of subclones used to assemble the entire genome will be less than about ten; will preferably be five or six, and alternatively about three or four. Subclones of a viral genome are generally obtained by first digesting a viral genome with one or more restriction enzymes that are selected according to the guidelines set forth herein. As set forth above, subclones may be amplified, purified, mutated, or otherwise treated by the practitioner to produce the desired subclone in the desired amount, form or sequence. In particular, unique junction sites for assembly of a full length cDNA clone may be created in the genome by techniques such as, for example, primer-mediated PCR mutagenesis (e.g., using specifically designed primer pairs). Such methods can be used to insert unique restriction sites at the 5' and 3' ends of each subclone. Preferably, these methods do not alter the coding sequence of the genome.

Numerous restriction enzymes and restriction enzyme sites (also referred to herein as "junctions") are, known in the art and can be used in methods of the present invention. The restriction site will preferably be staggered or "sticky," as these terms are understood in the art. In one embodiment of the invention, the restriction enzyme recognizes palindrome sequences, but leaves random sticky ends of one to four nucleotides in length that are not complementary to most other sticky ends generated with the same enzyme at other sites in the DNA. Preferably, the restriction site is unique within the genome; that is, digesting the genome with the enzyme will produce subsequences (i.e., subclones) of the genome wherein the terminus of each subclone may be ligated to only one of the termini of the adjacent subclone. Also preferably, the restriction enzyme site is recognized by a restriction enzyme that is "rare" or is a rare cutter; that is, the sequence that is recognized and cleaved by the enzyme occurs infrequently in any given genome. Restriction enzyme sites useful in the practice of the present invention include those sites recognized by restriction enzymes that include but are not limited to AccB71, Alw26I, Bgl1, BstX1, Not1, Sfi1, Sap1, Bbs1, Pflm1, Bbv1, EcoR1, Bsmf1, Eclhk1, Fok1, MboII, TthiIII, Ahdl, Drd1, Bspm1, Bsmb1, Bsma1, Bcg1, Bpm1, Bsa1, Bse1, Ear1, Alwn1, and DraIII. Preferred restriction enzymes are Bgl1, BstX1, Sfi1, Sap1, and Not1, with Bgl1 and BstX1 being particularly preferred.

The present invention finds use in the preparation of vaccines and expression vectors (e.g., TGE vectors and vaccines), as the polycistronic genome organization and synthesis of subgenomic length mRNAs allows for the simultaneous expression of one or more heterologous genes. The vectors may be targeted to other species by, for example, replacing the S glycoprotein gene. See Kuo, L., et al., *J. Virol.* 74, 1393–1406 (2000). The use of coronavirus expression vectors provides particular advantage in that intergenic sequences rarely overlap with upstream ORFs, simplifying the design and expression of heterologous genes from downstream intergenic promoters.

The present invention advantageously allows for the directional assembly of very large genomes. For example, the present invention can be used to construct fully functional genomes more than 20 kB in size, or more than 25 kB in size, or more than 30 kB in size, or more than 40 kB in size, or more than 50 kB in size, or more than 75 kB in size. The present invention may also be used to construct genomes more than 100 kB (e.g., 1 MB) in size, or more than 200 kB, or more than 300 kB in size, or even more than 400 kB in size. The assembly method of the present invention can be used to construct full-length infectious clones of, for example and without limitation, large RNA viruses including coronaviruses (27–32 kb), toroviruses (24–27 kb), and filoviruses like Ebola and Marburg (19 kb). Viral genomes that are unstable in prokaryotic vectors can also be successfully cloned using these methods. See, e.g., Boyer et al., supra, Rice et al., supra; and Sumyoshi, et al., supra.

Moreover, full length infectious double-stranded DNA (dsDNA) genomes of viruses (e.g., adenoviruses and herpesviruses) may be constructed and advantageously used in methods of vaccination, gene transfer and gene therapy. Historically, full length infectious clones of these DNA viruses have been generated by ligation of DNA fragments or by homologous recombination. Direct ligation of DNA fragments has been restricted by the low efficiency of large fragment ligations and the scarcity of unique restriction sites which make the approach technically challenging. Systematic and precise assembly according to the present invention using rare restriction enzymes ("cutters," e.g., Sfi1, Sap1) that leave variable ends and can be purposely engineered into a sequence should simplify assembly of large linear or circular dsDNA viruses. The approach of the present invention will generally alleviate the difficulties associated with typical restriction enzymes, or recombination approaches which often result in second site alterations. The inventive method may also circumvent other restrictions inherent in recombination-based methodologies that are limited to specific regions in the viral genome, and that often result in recombinant viruses which are not wildtype while allowing the introduction/removal of only a few genes in the virus vectors.

The skilled artisan will recognize that the present invention is not limited to manipulating the chromosomes of large RNA and DNA viruses.

Recently, the completion of the genome sequence of a large number of prokaryotic and eukaryotic (e.g., plant, animals) chromosomes has provided significant insight into gene organization, structure and function. The present method provides means to study the function of large blocks of DNA, like pathogenesis islands, or to directly engineer chromosomes that contain large gene cassettes of interest. These methods may also circumvent the limited cloning capacity and stability of viral vectors and plasmids used in the construction of mammalian or bacterial artificial chromosomes, and will simplify the manipulation of sequences in these large vectors.

The following Examples are provided to illustrate the present invention, and should not be construed as limiting thereof.

EXAMPLE 1

Virus and Cells

The Purdue strain (ATCC VR-763) of Transmissible Gastroenteritis Virus (TGE) was obtained from the American Type Culture Collection (ATCC) and passaged once in the swine testicular (ST) cell line. ST cells were obtained from the ATCC (ATCC 1746-CRL) and were maintained in minimal essential medium (MEM) containing 10% fetal clone II and supplemented with 0.5% lactalbumin hydrolysate, 1× nonessential amino acids, 1 mM sodium pyruvate, kanamycin (0.25 μg/ml) and gentamycin (0.05 μg/ml). Baby hamster kidney cells (BHK) were maintained in alpha MEM containing 10% fetal calf serum supplemented with 10% tryptose phosphate broth, kanamycin (0.25 μg/ml) and gentamycin (0.05 μg/ml). Wildtype TGE or TGE derived from the full-length clone were plaque purified twice, and stocks grown in ST cells as described in Sethna et al., (1989) and Sethna et al. (1991), supra. To measure the growth rate of different viruses, cultures of ST cells ($5\times10^5$) were infected with wildtype TGE or various infectious clone isolates at a multiplicity of infection (MOI) of 5 for 1 hr. The cells were washed 2× with PBS to remove residual virus and incubated at 37° C. in complete medium. At different times postinfection, progeny virions were harvested and assayed by plaque assay in ST cells.

EXAMPLE 2

Mutagenesis, Cloning and Sequencing of the TGE Genome

The TGE cloning strategy utilized in one embodiment of the present invention is illustrated in FIG. 1. The TGE genome was cloned from infected ST cell RNA by reverse transcription-polymerase chain reaction (RT-PCR) using primer pairs directed against the Purdue strain of TGE or a Taiwanese isolate. See, e.g., Chen, C. M., et al., *Virus Res.* 38, 83–89 (1997); Eleouet, J. F., et al., supra.; Racaniello, V. R. et al., Science 214, 916–919 (1981). To create unique junction sites for assembly of a full length TGE cDNA clone, primer-mediated PCR mutagenesis was used to insert unique restriction sites at the 5' and 3' ends of each subclone (see FIG. 9). These primer pairs do not alter the coding sequence and result in RT-PCR amplicons ranging in size from 1.5 to 6.3 KB in length. Total intracellular RNA was isolated from TGE-infected cells using RNA STAT-60 reagents according to the manufacturer's directions (Tel-TEST "B", Inc.). To isolate the TGE subclones, reverse transcription was performed using Superscript II™ and oliogdeoxynucleotide primer pairs according to the manufacturers recommendations (Gibco, BRL). Following cDNA synthesis at 50° C. for 1 hr, the cDNA was denatured for 2 mins at 94° C. and amplified by PCR with Expand Long TAQ polymerase (Boehringer Mannheim Biochemical) for 25 cycles of denaturation at 94° C. for 30 sec, 58° C. for 25–30 sec and 68° C. for 1–7 mins depending upon the size of the amplicon. The PCR amplicons were isolated from agarose gels and cloned into Topo II TA (Invitrogen) or pGem-TA cloning vectors (Promega) according to the manufacturer's directions.

Three to seven independent clones of each TGE amplicon were isolated and sequenced using a panel of primers located about 0.5 Kb from each other on the TGE insert and an ABI model automated sequencer. A consensus sequence for each of the cloned fragments was determined, and when necessary (i.e., pTGE A, pTGE B1, pTGE C and pTGE F) a consensus clone was assembled using restriction enzymes and standard recombinant DNA techniques to remove unwanted amino acid changes associated with reverse transcription or naturally occurring quasispecies variation.

EXAMPLE 3

Assembly of a Full Length TGE Infectious Clone

Each of the plasmids were grown to high concentration, isolated and digested, or double-digested, with Bgl1, BstX1 or Not1 according to the manufacturers direction (NEB) (FIG. 1A). The TGE A clone was digested with Apa1, treated with calf alkaline phosphatase, and then Bgl1 digested, resulting in a approximately 6.3 Kb fragment. The TGE F clone was Not 1 digested, treated with calf alkaline phosphatase, and then Bgl 1 digested. All other vectors were digested with Bgl1 or Bst X1. The appropriately-sized cDNA insert was seperated on 0.8–1.2% agarose gels in TAE buffer (Tris-acetate, EDTA) containing 5 mM cytidine (Fluka) and then extracted using Qiaex II gel extraction kits according to the manufacturer's directions (Qiagen Inc, Valencia, Calif.). Cytidine was incorporated to reduce DNA damage associated with cumulative UV exposure during visualization in agarose gels. Appropriate cDNA subsets (A+B1), (B2+C), (DE-1+F) were pooled into 100 to 300 $\mu$l aliquots, and equivalent amounts of each DNA were ligated with T4 DNA ligase (15 U/100 $\mu$l) at 16° C. overnight in 30 mM Tris-HCl (pH 7.8), 10 mM $MgCl_2$, 10 mM DTT and 1 mM ATP. Appropriately-sized products (AB1+B2C+DE–1F) were separated in 0.7% agarose gels containing 5 mM cytidine as described, isolated and religated as described above. The final products were purified by phenol chloroform isoamyl alcohol (1:1:24) and chloroform extraction and then precipitated under ethanol prior to in vitro transcription reactions. The full length TGE construct is designated TGE 1000.

It has been reported that the nucleocapsid protein may function as part of the transcriptional complex. To provide N protein in trans, the TGE N gene was amplified from the TGE F clone using primer pairs flanking the N gene ORF. The upstream primer had a SP6 site: (5'-TCGGCCTCGATTTAGGTGACA CTATAGATGGCCAACCAGGGACAACG-3'; SEQ ID NO:3) while the downstream primer introduced a 14 nucleotide oligo T stretch providing a poly A tail following in vitro transcription: (5'-TTTTTTTTTTTTTTAGTTCGT TACCTC GTCAATC-3'; SEQ ID NO:4). The TGE leader RNA sequence, 3'-most ORE and noncoding sequences were not present within this construct. PCR product was purified from gels and used directly for in vitro transcription.

EXAMPLE 4

RNA Transfection

Full-length transcripts of the TGE cDNA, TGE 1000, were generated in vitro as described by the manufacturer (Ambion, mMessage mMachine; Austin, Tex.) with certain modifications. For two hours at 37° C., several 30 $\mu$l reactions were performed that were supplemented with 4.5 $\mu$l of a 30 mM GTP stock that resulted in a 1:1 ratio of GTP to cap analog. Similar reactions were performed using 1 $\mu$g of PCR amplicons encoding the TGE N gene sequence or Sindbis virus noncytopathic replicons encoding green fluorescent protein (pSin-GFP, kindly provided by C. Rice, Washington University) and a 2:1 ratio of cap analog to GTP. One tenth of the transcripts were denatured and separated in 0.5% agarose gels in TAE buffer containing 0.1% SDS. The remainder of each sample was either treated with 50 ng of RNAse A for 15 mins at room temperature, or directly electroporated into BHK cells.

BHK or ST cells were grown to subconfluence, trypsinized, washed 2× with PBS and resuspended in PBS at a concentration of $10^7$ cells/ml. RNA transcripts were added to 800 $\mu$l of the cell suspension in an electroporation cuvette and three electrical pulses of 850 V and 25 $\mu$F were given with a BioRAD Gene Pulser II electroporator. The BHK cells were seeded with $1.0 \times 10^6$ uninfected ST cells in a 75 $cm^2$ flask and incubated at 37° C. for 3–4 days. Virus progeny were then passaged in ST cells in 75 $cm^2$ flasks at two day intervals and twice purified by plaque assay.

EXAMPLE 5

Immunofluorescence Assays

Cells were grown on LabTek chamber slides (4 or 8 well) and were either infected with wildtype TGE, or progeny virions generated from the infectious construct, which had been serially passaged in ST cells. At 12 hrs postinfection, cells were fixed in acetone-methanol (1:1) and stored at 4° C. Fixed cells were rehydrated in PBS (phosphate buffered saline, pH 7.2) and then incubated with a 1:100 dilution of mouse anti TGE polyclonal antiserum for 30 mins at room temperature. After three washes in PBS, the cells were incubated with a 1:100 dilution of goat anti-mouse immunoglobulin G fluorescein isothiocyanate (FITC) conjugate (Sigma) for 30 min at room temperature. After three additional washes with PBS, the cells were visualized and photographed under a Nikon FXA fluorescence microscope. Images were digitized and assembled in Photoshop 5.5 (Adobe Systems Inc.).

EXAMPLE 6

RT-PCR to Detect Marker Mutations and Sequence Analysis

Cultures of ST cells were infected for 1 hr at room temperature with wildtype TGE, or plaque purified icTGE-1 and icTGE-3 viruses that were derived from the infectious construct. Intracellular RNA was isolated at 12 hrs postinfection and used as template for RT-PCR reactions using four different primer pair sets that asymmetrically flank each of the interconnecting Bgl1 or BstX1 junctions that were used in the assembly of TGE 1000. RT reactions were performed using Superscript II reverse transcriptase for 1 hr at 50° C. prior to PCR amplification with the reverse primer that flanked the different interconnecting junctions. To amplify across the B1/B2 junction, forward (5'-GCATCGTAAGACTCAACAAGG-3'; SEQ ID NO:5) and reverse (5'-GTCACAGCAAGTGAGAACCATG-3'; SEQ ID NO:6) primers were located at nucleotides 9738–9759 and 10270–10248, respectively and resulted in a 532 bp amplicon. In virus derived from the infectious construct, BstX1 digestion should result in 321 and 221 bp fragments. To amplify across the B2/C junction, forward (5'-TTGAGCGCGAAGCATCAGTGC-3'; SEQ ID NO:7) and reverse (5'-TTCCACTGCCGAAAGCTTCACC-3'; SEQ ID NO:8) primers were located at nucleotides 11231–11151 and 11655–11634, and result in an amplicon of 424 bp. In virus derived from infectious construct, Bgl1 digestion should result in products of 300 and 124 bp in length. To amplify across the C/DE junction, forward (GAATGTGCACACTAGGACCTG; SEQ ID NO:9) and reverse (AGCAGGTGGTATGTATTGTTCG; SEQ ID NO:10) primers were located at nucleotides 16,380–16400 and 16,936–16957, respectively. See Eleouet et al., supra. If a Bgl1 site is present in this 577 bp amplicon, digestion should result in products of 370 and 207 bp in length. To amplify across the DE/F junction, forward (CGTTGTACAGGTGGTTATGAc; SEQ ID NO:11) and reverse (CTCCGCTTGTCTGGTTAGAGTC. SEQ ID NO:12) primers were located at nucleotides 23304–23324 and 23852–23873 in the S gene, respectively. Following Bgl1 digestion of this 549 bp amplicon, a 386 and 163 bp fragment should be visualized in viruses derived from the infectious construct. Following 28 cycles of amplification with Taq polymerase, the PCR products were separated and isolated from agarose gels. POR amplicons were either subcloned directly into pGemT cloning vectors for sequencing, or digested with Bgl1 or BstX1 restriction endonucleases according to the manufacturer's directions (NEN). The digested DNAs were then separated in 1.5% agarose gels in TAE buffer and visualized under UV light. All sequence comparisons were performed with the Vector Suite II (Informax Inc) using Align X programs.

EXAMPLE 7

Assembly of a Full Length TGE Clone

Initially, five cDNA subclones spanning the entire TGE genome (designated TGE A, B, C, D, E and F) were isolated. Each cDNA clone is flanked by unique Bgl1 sites and will only anneal with the appropriate adjacent subclone, resulting in a full-length TGE construct (FIG. 1A). To RT-PCR clone the 6.2 Kb TGE A fragment located at the 5' end of the TGE genome, the forward primer included a T7 start site and the 5'-most TGE leader RNA sequences while the reverse primer was located at nucleotide 6180, just downstream from a naturally occurring Bgl1 site (GCCTGTT↓TGGC; SEQ ID NO:13) in the TGE genome. (See Elеouet et al., supra; FIG. 9). The 5.2 Kb B fragment was amplified using a forward primer upstream of the Bgl1 site at position 6159 and at a reverse primer which introduced a unique Bgl1 site (GCCGCAT↓CGGC; SEQ ID NO:14) at position 11,355 (FIG. 1). The 5.2 Kb C fragment was amplified using a forward primer which introduced the same Bgl1 site at nucleotide 11,355 and a reverse primer which introduced another unique Bgl1 site (GCCTTCT↓TGGC; SEQ ID NO:15) at position 16,587. The original cloning strategy called for separate D and E fragments; however, it became evident that a single 6.9 Kb fragment was stable in microbial vectors. Therefore, a single DE fragment was amplified using a forward primer that introduced the same Bgl1 site at position 16,587 and a reverse primer which introduced a new Bgl1 site (GCCGTG↓AGGC; SEQ ID NO:16) in the S glycoprotein gene at nucleotide 23,487. The F fragment was cloned with a forward primer which introduced the same Bgl1 site at position 23,487 and a reverse primer that contained the 3'-most nucleotides of the TGE genome including an additional 25T's prior to terminating at a Not1 site. A list of the primers used to mutagenize the TGE genome and to isolate each of the TGE subclones is shown in FIG. 9. These primer pairs did not alter the amino acid sequence of the virus. The sequence of the unique interconnecting junctions is shown in Table 2. Restriction enzymes that cleave at specific sites and leave multiple sticky ends are shown in Table 1.

TABLE 1

| Restriction Enzyme | Palindromic Site | Variable Sticky End | Cutting Frequency[1] | Actual Compatible End Frequency[2] | |
|---|---|---|---|---|---|
| AccB71 | CCANNNN↓NTGG<br>GGTN↓NNNNACC | 3 | 4096 | 261,344 | SEQ ID NO:17 |
| Alw261 | GTCTCN↓NNNN<br>CTGAGNNNNN↓ | 4 | 1024 | 261,344 | SEQ ID NO:18 |
| Bgl1 | GCCNNNN↓NGGC<br>CGGN↓NNNNCCG | 3 | 4096 | 261,344 | SEQ ID NO:1 |
| BstX1 | CCANNNNN↓NTGG<br>GGTN↓NNNNNACC | 4 | 4096 | 1,045,376 | SEQ ID NO:19 |
| Sfi1 | GGCCNNNN↓NGGCC<br>CCGGN↓NNNNCCGG | 3 | 65,336 | 4,181,504 | SEQ ID NO:2 |

TABLE 1-continued

| Restriction Enzyme | Palindromic Site | Variable Sticky End | Cutting Frequency[1] | Actual Compatible End Frequency[2] | |
|---|---|---|---|---|---|
| Sap1 | GCTCTTCN↓NNN<br>CGAGAAGNNNN↓ | 3 | 16,385 | 4,181,504 | SEQ ID NO:20 |
| Bbs1 | GAAGACNN↓NNN<br>CTTCTGNNNNNN↓ | 4 | 4096 | 1,045,376 | SEQ ID NO:21 |
| Pflm1 | CCANNNN↓NTGG<br>GGTN↓NNNNACC | 3 | 4096 | 261,344 | SEQ ID NO:22 |
| Bbv1 | GCAGCNNNNNNNN↓NNNN<br>CGTCGNNNNNNNNNNNN↓ | 4 | 1024 | 261,344 | SEQ ID NO:23 |
| EcoR1 | G↓AATTC<br>CTTAA4↓G | 4 | 4096 | 4,096 | |

[1]AVERAGE FREQUENCY OF THE RESTRICTION SITE APPEARING IN A GENOME (IN BASE PAIRS),
[2]FREQUENCY WITH WHICH A COMPATIBLE END IS ACTUALLY GENERATED (IN BASE PAIRS),
[3]OTHER ENZYMES LEAVING VARIABLE ENDS: BSMF1, ECLHK1, FOK1, MBOII TTHIIII, AHD1, DRD1, BSPM1, BSMB1, BSMA1, BCG1, BMR1, BPM1, BSA1, BSE1, EAR1, ALWN1, DRAIII

TABLE 2

| Site | Interconnecting Junction | Restriction Site | |
|---|---|---|---|
| A/B1 Junction<br>nt 6159 | 5'-GCCT**GTT**↓ TGGC-3'<br>3'-CGGA↑ **CAA**ACCG-5' | Bgl 1 | SEQ ID NO:13 |
| wt | C | | |
| B1/B2 Junction<br>nt 9950 | 5'-CCAT**TCAC**↓ TTGG-3'<br>3'-GGTA↑ **AGTG**AACC-5' | Bxt X1 | SEQ ID NO:24 |
| wt | T A | | |
| B2/C Junction<br>nt 11,355 | 5'-GCCG**CAT**↓ CGGC-3'<br>3'-CGGC↑ **GTA**GCCG-5' | Bgl 1 | SEQ ID NO:14 |
| wt | T A | | |
| C/DE-1 Junction<br>nt 16,587 | 5'-GCCT**TCT**↓ TGGC-3'<br>3'-CGGA↑ **AGA**ACCG-5' | Bgl 1 | SEQ ID NO:15 |
| wt | A T | | |
| DE-1/F Junction<br>nt 23,4873 | 5'-GCCG**TGC**↓ AGGC-3'<br>3'-CGGC↑ **ACG**TCCG-5' | Bgl 1 | SEQ ID NO:16 |

The pTGE A, C, DE and F clones were stable in plasmid DNA's in *E.coli*. The B fragment, however, was unstable and only a few slow growing isolates were obtained, all of which contained deletions or insertions in the wild-type sequence. During two different cloning attempts, a 200–300 nucleotide fragment from the *E.coli* chromosome was inserted at position 9973, which corresponds to a region of instability in the TGE genome noted by other investigators (FIG. 1B; see J. F. Eleouet, *Virology* 206, 817–822 (1995)). In addition, some clones contained an approximately 500 bp deletion across this domain. It was assumed that breaks in the TGE B sequence at or around nucleotide 9973 might detoxify fragment instability and allow the cloning of these sequences into *E.coli*. Since the TGE B fragment did not contain a BstX1 site, primer-mediated mutagenesis was used to bisect the B fragment into TGE B1 and TGE B2 amplicons with an adjoining BstX1 (CCATTCA↓TTGG; SEQ ID NO:24) site located at position 9950 in the TGE genome (Table 2). The four nucleotide overhang generated by BstX1 would also provide additional specificity and sensitivity in systematically assembling the TGE subclones. After these modifications, pTGE B1 and B2 plasmid subclones were rapidly identified which were stable and grew efficiently in *E.coli*. The location of each of the subclones used in the assembly of the TGE full-length clone is shown in relationship to important motifs or cis-acting sequences in the viral genome (FIG. 2).

Inserts from three to six independent clones from each fragment were sequenced and a consensus TGE subclone was assembled using standard recombinant DNA techniques. The consensus sequence of our Perdue TOE full-length clone contained 14 amino acid changes and numerous silent changes as compared with the published sequence (FIG. 2). In addition, perfect T7 RNA polymerase termination sites were identified in the consensus sequence at nucleotides 3635 in the pTGE A subclone and 13,618 in the pTGE C subclone, and were removed by primer-mediated overlapping POR mutagenesis without altering the coding sequence. See Eleouet et al., supra.

To assemble a full-length cDNA construct of TOE, plasmids were digested with Bgl1, BstX1 or Not1 and the appropriate-sized inserts were isolated from agarose gels (FIG. 3A). The TGE A and B1, B2 and C, and the DE-1 and F fragments were ligated overnight in the presence of T7 DNA ligase. Systematically assembled products were isolated from agarose gels (FIGS. 3B–D), and the TOE A/B1, B2/C3-2, DE-1/F fragments religated overnight. The final products were purified by phenol/chloroform isoamyl alcohol, chloroform extraction, precipitated under ethanol and then separated in agarose gels (FIG. 4A). An appropriately sized full-length TGE cDNA of about 29 Kb in length (TOE 1000) was clearly apparent, as were some assembly intermediates. Capped-T7 transcripts were synthesized and 1/10 of the product analyzed in 0.5% agarose gels in parallel with TOE 1000 assembled product. These data demonstrate that low levels of full-length transcripts of the appropriate size were evident following T7 transcription in vitro (FIG. 4B). DNase treatment removed the TGE full-length cDNA as well as minor assembly intermediates (FIG. 4B).

EXAMPLE 8

Transfection and Recovery of Infectious Virus

Synthesis of full-length TGE transcripts has proven difficult and resulted in little full length RNA product (FIG. 4B). To address this problem, several different strategies were tested to maximize infectivity of the full length transcripts in vitro. Under identical conditions of treatment, about 10–20% of the ST cells are efficiently transfected with Sindbis replicons encoding GFP, as compared with about 60–80% of the BHK cells (data not shown). As coronavirus host range specificity occurs primarily at entry and the genomic RNA is infectious in a variety of permissive and nonpermissive cells (see Baric, R. S. et al., *J. Virology* 71, 638–649 (1999)), it was surmised that BHK cells might be more sensitive primary hosts because of the intrinsically higher transfection efficiency. In addition, several reports have also indicated that the coronavirus N nucleocapsid protein functions as part of the transcription complex, and might enhance infectivity of full length transcripts. See Baric, R. S., et al., *J. Virol.* 62, 4280–4287 (1988). Consequently, four different transfection strategies were tested in BHK cells.

BHK cells were transfected with TGE transcripts alone, TGE+TGE N gene transcripts, or just TGE N transcripts. In a parallel experiment, TGE+TGE N gene transcripts were pretreated with Rnase A prior to transfection. Following electroporation, the BHK cells were seeded with $1.0\times10^6$ ST cells to serve as appropriate permissive hosts for progeny virus amplification.

Three days post-transfection, supernatants were passaged into ST cells and CPE was observed within 36 hrs postinfection only with supernatants derived from the TGE+N transfected cultures. Supernatants were harvested at 48 hrs postinfection and passaged twice more at 48 hr intervals in fresh ST cell cultures. CPE, typical of TGE infection, was evident at each passage (data not shown). Fluorescent antibody staining with mouse anti-TGE serum demonstrated that viral antigen was clearly present in each passage (FIG. 5). Using RT-PCR with primer pairs located within the leader RNA sequence and at the 3' end of the TGE genome, leader-containing subgenomic mRNA transcripts (mRNA 6 and 7) encoding the N and hydrophobic membrane proteins were also evident in passage 1 ST cells (data not shown). Furthermore, virus derived from the TGE 1000 transcripts was diluted and inoculated into ST cells where plaques developed after 48 hrs postinfection (FIG. 6). TGE+N transcripts-treated with RNase A prior to electroporation did not result in the production of infectious virus.

Plaque purified stocks, prepared from passages 1 through 3 (icTGE-1, icTGE-2, icTGE-3), were used in growth curves and compared to the parental TGE strain in ST cells. Cultures were infected with virus at a MOI of 5 for 1 hr and samples harvested at selected times over the next 44 hrs. No significant differences in the replication of wildtype TGE or TGE 1000 derived viruses icTGE-1, icTGE-2 or icTGE-3 were noted in ST cells, and all viruses replicated to titers that approached $1\times10^8$ PFU/ml within 28 hrs (FIG. 7).

EXAMPLE 9

Identification of Marker Mutations

Infectious virus derived from transfected cultures should contain the four unique interconnecting junction sequences used in the construction of the infectious TGE 1000 construct (FIGS. 1 and 2). If these mutations produce a neutral phenotype on virus replication, they should also be stable during passage. Consequently, wildtype TGE, icTGE-1 and icTGE-3 were inoculated into ST cells and intracellular RNA isolated at 12 hrs postinfection. Using RT-PCR and primer pairs that asymmetrically flank each of the B1/B2, B2/C, C/DE-1 and DE-1/F junctions, products of approximately400–600 bp in length were amplified (FIG. 8). Results using restriction fragment length polymorphism (RFLP) analysis demonstrated that none of the marker mutations were present in the wildtype TGE genome (FIG. 8A). However, icTGE-1 and icTGE-3 both contained the unique marker mutation profiles used to create the unique Bgl1 and BstX1 restriction sites within the TGE 1000 construct (FIGS. 8B, C). The PCR products were subcloned and sequenced, and the determined sequence of the reverse complement of the sequence demonstrated that the appropriate mutations were present in the viruses isolated from the infectious construct. TGE 1000 transcripts were clearly infectious and produced virus which contained the appropriate marker mutations. These data illustrate that infectious constructs of coronaviruses can be systematically and precisely assembled from a series of smaller subclones in vitro.

In summary, a simple and rapid approach to systematically assemble a full-length infectious coronavirus cDNA from a panel of six smaller subclones was carried out. Evidence from several experiments demonstrated that the in vitro transcripts of the TGE 1000 genomic construct were infectious. Transcripts treated with RNase were not infectious, indicating that infection was likely initiated from the RNA transcripts synthesized in the in vitro transcription reaction. Media from transfected cultures could be used to propagate infection with corresponding cytopathology and viral antigen expression in fresh cultures of cells. Progeny virions formed plaques in monolayers of permissive cells, and plaque purified virus grew efficiently to levels equivalent with wildtype virus in permissive host cells. Most importantly, plaque purified virus contained the expected Bgl1 and BstX1 marker mutations, providing definitive evidence that transcripts from the TGE 1000 construct were infectious in vitro. The presence of these mutations does not restrict the ability of icTGE to replicate efficiently in ST cells.

Advantageously, the assembly strategy of the present invention for coronavirus infectious constructs does not use BAC vectors. The inventive method is also not dependent upon the availability of a preexisting viral DI cDNA clone as foundation for building the infectious clone. In contrast to infectious clones of other positive strand RNA viruses, the TGE 1000 construct must be reassembled de novo and does not exist intact in bacterial vectors, circumventing problems in sequence instability. This does not restrict its applicability for reverse genetic applications, but rather, allowed for genetic manipulation of independent subclones without introducing spurious mutations elsewhere in the genome during recombinant DNA manipulation.

Another advantage of the inventive approach is that different combinations of restriction sites can be used that generate highly variable 5' or 3' overhangs of one to four nucleotides in length, further increasing the specificity and sensitivity of the assembly cascade (FIG. 9). Because of insert toxicity in *E.coli,* infectious clones of yellow fever virus and Japanese encephalitis virus are assembled in vitro from two subclones but use conventional restriction enzymes like BamH1, Apa1 or Aat1. The present invention, however, prevents spurious self-assembly of subclones. This approach also provides an alternative to engineering large RNA or DNA genomes in BAC vectors which may be unstable, or may be extensively spliced in the nucleus. The present invention demonstrates that the unstable sequences can be disabled by bisecting the sequence between nucleotides 9758–9950 in the TGE genome. This information permits the isolation of larger TGE A/B1, B2/C and DE/F subclones, allows for the assembly of infectious cDNAs following a single DNA isolation/ligation step, and facilitates the localization of similar unstable sequences in other group 1 and 2 coronaviruses.

The foregoing is illustrative of the present invention and is not to be construed as limiting thereof. The invention is defined by the following claims, with equivalents of the claims to be included therein.

That which is claimed is:

1. A method of directionally assembling a recombinant viral genome, comprising:

obtaining a set of subclones of the viral genome, wherein each termini of each subclone is a restriction enzyme recognition site; and then ligating the subclones to assemble a recombinant viral genome.

2. The method of claim 1, wherein the recombinant viral genome is a full-length viral genome.

3. The method of claim 1, wherein the recombinant viral genome is capable of infecting a permissive host cell.

4. The method of claim 1, wherein the viral genome is a Nidovirus genome.

5. The method of claim 1, wherein the viral genome is a coronavirus genome.

6. The method of claim 1, wherein the viral genome is a transmissible gastroenteritis virus genome.

7. The method of claim 1, wherein the restriction enzyme recognition site is a site recognized by a restriction enzyme selected from the group consisting of AccB71, Alw26l, Bgl1, BstX1, Sfi1, Sap1, Bbs1, Pflm1, Bbv1, Bsmf1, EcIhk1, Fok1, MboII, TthiIII, Ahdl, Drd1, Bspm1, Bsmb1, Bsma1, Bcg1, Bpm1, Bsa1, Bse1, Ear1, Alwn1, and DraIII.

8. The method of claim 7, wherein the restriction enzyme recognition site is a site recognized by Bgl1.

9. The method of claim 7, wherein the restriction enzyme recognition site is a site recognized by BstX1.

10. The method of claim 1, wherein the viral genome is larger than 20 KB in length.

11. The method of claim 1, wherein the viral genome is larger than 25 kB in length.

12. The method of claim 1, wherein the viral genome is larger than 30 kB in length.

13. The method of claim 1, wherein the sequence of the recombinant viral genome comprises a mutation such that the nucleotide sequence of the recombinant viral genome differs from the nucleotide sequence of the wild type viral genome.

14. The method of claim 1, wherein the subclones comprise cDNA.

15. The method of claim 1, wherein the recombinant viral genome is an RNA genome.

16. The method of claim 1, wherein the recombinant viral genome is a DNA genome.

17. The method of claim 1, wherein the recombinant viral genome comprises a heterologous nucleic acid sequence.

18. The method of claim 1, wherein the set of subclones comprises at least three subclones.

19. The method of claim 1, wherein the set of subclones comprises at least five subclones.

20. A recombinant viral genome produced by the method of claim 1.

21. A recombinant viral genome comprising a set of subclones, wherein each subclone has a 3' terminus and 5' terminus comprising a restriction enzyme recognition site, and wherein each terminus is ligated to the terminus of the adjacent subclone to form a junction, and wherein each junction has a unique nucleic acid sequence.

22. The genome of claim 21, wherein the set of subclones comprises at least three subclones.

23. The genome of claim 21, wherein the set of subclones comprises at least five subclones.

24. A method of infecting a host cell with a recombinant viral genome, comprising contacting the host cell with a viral genome that has been assembled from a set of subclones and wherein the terminus of each subclone is a restriction enzyme recognition site, and wherein each subclone is ligated to the adjacent subclone such that the viral genome is directionally assembled and infective.

25. The method of claim 24, wherein the viral genome is a TGE genome.

26. The method of claim 1, wherein the restriction enzyme recognition site is a substrate for a restriction enzyme that produces random sticky ends after cleavage of the restriction enzyme recognition site.

27. The method of claim 1, wherein the subclones are each embedded within a plasmid vector and wherein the method further comprises the step of digesting the plasmid vectors comprising the subclones with a restriction enzyme that cleaves at the restriction enzyme recognition sites to excise the subclones from the plasmid vectors.

28. The method of claim 1, wherein the subclones are amplification products.

29. The method of claim 28, wherein the subclones are PCR amplification products and wherein the restriction enzyme recognition sites have been added to the subclones by primer-mediated PCR mutagenesis.

30. The method of claim 1, wherein the recombinant viral genome is selected from the group consisting of a recombinant human papilloma virus, lentivirus, enterovirus, hepatitis C virus, influenza virus, herpesvirus, mononegavirales, alphavirus, calcivirus, rotavirus, torovirus, filovirus, flavivirus and adenovirus genome.

31. A method of directionally assembling a recombinant viral genome, comprising:

obtaining a set of at least three subclones representing the viral genome, wherein each termini of each subclone is a single-stranded sticky end that is only complementary within a recursive assembly pathway to a sticky end of a subclone representing an adjacent portion of the genome; and then ligating the subclones to directionally assemble a recombinant viral genome.

32. The method of claim 31, wherein the recombinant viral genome is a full-length viral genome.

33. The method of claim 31, wherein one or more of the sticky ends is produced by a restriction enzyme selected from the group consisting of AccB71, Alw26l, Bgl1, BstX1, Sfi1, Sap1, Bbs1, Pflm1, Bbv1, Bsmf1, Eclhk1, Fok1, MboII, TthiIII, Ahdl, Drd1, Bspm1, Bsmb1, Bsma1, Bcg1, Bpm1, Bsa1, Bse1, Ear1, Alwn1, and DraIII.

34. The method of claim 31, wherein one or more of the sticky ends is produced by a restriction enzyme selected from the group consisting of Bgl1, BstX1, Sf1, and Sap1.

35. The method of claim 31, wherein the viral genome is larger than 20 KB in length.

36. The method of claim 31, wherein the sequence of the recombinant viral genome comprises a mutation such that the nucleotide sequence of the recombinant viral genome differs from the nucleotide sequence of the wild type viral genome.

37. The method of claim 31, wherein the recombinant viral genome comprises a heterologous nucleic acid sequence.

38. The method of claim 31, wherein the recombinant viral genome is selected from the group consisting of a recombinant human papilloma virus, lentivirus, enterovirus, hepatitis C virus, influenza virus, herpesvirus, mononegavirales, alphavirus, calcivirus, rotavirus, torovirus, filovirus, flavivirus and adenovirus genome.

39. A method of directionally assembling a recombinant coronavirus genome, comprising:

obtaining a set of at least three subclones representing the genome, wherein each termini of each subclone is a single stranded sticky end that only complementary within a recursive assembly pathway to a sticky end of a subclone representing an adjacent portion of the genome; and then ligating the subclones to directionally assemble a recombinant genome.

40. The method of claim 39, wherein the recombinant viral genome is a full-length viral genome.

41. The method of claim 39, wherein one or more of the sticky ends is produced by a restriction enzyme selected from the group consisting of AccB71, Alw26l, Bgl1, BstX1, Sfi1, Sap1, Bbs1, Pflm1, Bbv1, Bsmf1, EcIhk1, Fok1, MboII, TthiIII, Ahdl, Drd1, Bspm1, Bsmb1, Bsma1, Bcg1, Bpm1, Bsa1, Bse1, Ear1, Alwn1, and DraIII.

42. The method of claim 39, wherein one or more of the sticky ends is produced by a restriction enzyme selected from the group consisting of Bgl1, BstX1, Sfi1, and Sap1.

43. The method of claim 39, wherein the sequence of the recombinant viral genome comprises a mutation such that the nucleotide sequence of the recombinant viral genome differs from the nucleotide sequence of the wild type viral genome.

44. The method of claim 39, wherein the recombinant viral genome comprises a heterologous nucleic acid sequence.

45. A method of directionally assembling a recombinant transmissible gastroenteritis virus genome, comprising:

obtaining a set of at least three subclones representing the genome, wherein each termini of each subclone is a single-stranded sticky end that is only complementary within a recursive assembly pathway to a sticky end of a subclone representing an adjacent portion of the genome; and then ligating the subclones to directionally assemble a recombinant genome.

46. The method of claim 45, wherein the recombinant viral genome is a full-length viral genome.

47. The method of claim 45, wherein one or more of the sticky ends is produced by a restriction enzyme selected from the group consisting of AccB71, Alw26l, Bgl1, BstX1, Sfi1, Sap1, Bbs1, Pflm1, Bbv1, Bsmf1, Eclhk1, Fok1, MboII, TthiIII, Ahdl, Drd1, Bspm1, Bsmb1, Bsma1, Bcg1, Bpm1, Bsa1, Bse1, Ear1, Alwn1, and DraIII.

48. The method of claim 45, wherein one or more of the sticky ends is produced by a restriction enzyme selected from the group consisting of Bgl1, BstX1, Sf1, and Sap1.

49. The method of claim 45, wherein the sequence of the recombinant viral genome comprises a mutation such that the nucleotide sequence of the recombinant viral genome differs from the nucleotide sequence of the wild type viral genome.

50. The method of claim 45, wherein the recombinant viral genome comprises a heterologous nucleic acid sequence.

51. A recombinant viral genome produced by the method of claim 31.

52. A recombinant coronavirus genome produced by the method of claim 39.

53. A recombinant transmissible gastroenteritis virus genome produced by the method of claim 45.

* * * * *

UNITED STATES PATENT AND TRADEMARK OFFICE

CERTIFICATE OF CORRECTION

PATENT NO. : 6,593,111 B2
DATED : July 15, 2003
INVENTOR(S) : Baric et al.

It is certified that error appears in the above-identified patent and that said Letters Patent is hereby corrected as shown below:

Column 29,
Line 17, should read -- from the group consisting of Bgl1, BstX1, Sfi1, and Sap1. --
Line 38, should read -- single-stranded sticky end that is only complementary --

Column 30,
Line 34, should read -- from the group consisting of Bgl1, BstX1, Sfi1, and Sap1. --

Signed and Sealed this

Twenty-fourth Day of February, 2004

JON W. DUDAS
*Acting Director of the United States Patent and Trademark Office*